US012338433B2

(12) United States Patent
Dong et al.

(10) Patent No.: US 12,338,433 B2
(45) **Date of Patent: *Jun. 24, 2025**

(54) MODIFIED NUCLEIC ACIDS, HYBRID GUIDE RNAS, AND USES THEREOF

(71) Applicant: OHIO STATE INNOVATION FOUNDATION, Columbus, OH (US)

(72) Inventors: Yizhou Dong, Dublin, OH (US); Bin Li, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,827

(22) Filed: Dec. 18, 2023

(65) Prior Publication Data

US 2024/0229011 A1 Jul. 11, 2024

Related U.S. Application Data

(63) Continuation of application No. 16/316,135, filed as application No. PCT/US2017/041133 on Jul. 7, 2017, now Pat. No. 11,845,929.

(60) Provisional application No. 62/480,716, filed on Apr. 3, 2017, provisional application No. 62/359,880, filed on Jul. 8, 2016.

(51) Int. Cl.

| | |
|---|---|
| ***C12N 9/22*** | (2006.01) |
| ***C12N 15/10*** | (2006.01) |
| ***C12N 15/113*** | (2010.01) |
| ***C12N 15/90*** | (2006.01) |

(52) U.S. Cl.

CPC ............. *C12N 15/102* (2013.01); *C12N 9/22* (2013.01); *C12N 15/113* (2013.01); *C12N 15/90* (2013.01); *C12N 2310/113* (2013.01); *C12N 2310/20* (2017.05); *C12N 2310/315* (2013.01); *C12N 2310/321* (2013.01); *C12N 2310/322* (2013.01); *C12N 2310/3521* (2013.01); *C12N 2310/3533* (2013.01)

(58) Field of Classification Search

None

See application file for complete search history.

(56) References Cited

U.S. PATENT DOCUMENTS

| | | | |
|---|---|---|---|
| 9,650,617 | B2 | 5/2017 | May |
| 2015/0071901 | A1 | 3/2015 | Liu |
| 2015/0232881 | A1 | 8/2015 | Glucksman et al. |
| 2016/0215300 | A1 | 7/2016 | May |

FOREIGN PATENT DOCUMENTS

| | | | |
|---|---|---|---|
| WO | 2015168404 | 11/2015 | |
| WO | 2016094867 | 6/2016 | |
| WO | 2016100562 | 6/2016 | |
| WO | WO-2016094867 A1 * | 6/2016 | ......... A01K 67/0275 |
| WO | 2016123230 | 8/2016 | |
| WO | 2017004261 | 1/2017 | |

OTHER PUBLICATIONS

Koonin et al., Diversity, classification and evolution of CRISPR-Cas systems. Current Opinion in Microbiology (2017), 37:67-78 (Year: 2017).*

Nishimasu and Nureki, Structures and mechanisms of CRISPR RNA-guided effector nucleases. Current Opinion in Structural Biology (2017), 43: 68-78 (Year: 2017).*

Jackson et al., Crystal structure of the CRISPR RNA-guided surveillance complex from *Escherichia coli*. Science (2014), 1473-1479. (Year: 2014).*

Jinek et al., A Programmable Dual-RNA-Guided DNA Endonuclease in Adaptive Bacterial Immunity. Science (2012), 337: 816-821 (Year: 2012).*

Dorsey et al., Structural organization of a Type III-A CRISPR effector subcomplex determined by X-ray crystallography and cryo-EM. Nucleic Acids Research (2019), 47(7): 3765-3783 (Year: 2019).*

Zetsche et al., Cpf1 Is a Single RNA-Guided Endonuclease of a Class 2 CRISPR-Cas System. Cell (2015), 163: 759-771. (Year: 2015).*

Shmakov et al., Discovery and Functional Characterization of Diverse Class 2 CRISPR-Cas Systems. Molecular Cell (2015), 60: 385-397. (Year: 2015).*

Yan et al., Functionally diverse type V CRISPR-Cas systems. Science (2019), 363: 88-91 (Year: 2019).*

Abudayyeh et al., C2c2 is a single-component programmable RNA-guided RNA-targeting CRISPR effector. Science (2016), 353 (6299): aaf5573, 1-9. (Year: 2016).*

Rahdar et al., Synthetic CRISPR RNA-Cas9-guided genome editing in human cells. PNAS (2015), E7110-E7117 (Year: 2015).*

Zetsche et al., Cpf1 is a single RNA-guided endonuclease of a class 2 CRISPR-Cas system. Cell (2016) 163: 759-771 (Year: 2015).*

Altschul et al. (1977) Gapped BLAST and PSI-BLAST: a new generation of protein database search programs, Nuc. Acids Res. 25:3389-3402.

Altschul et al. (1990) Basic Local Alignment Search Tool, J. Mol. Biol. 215:403-410.

Beaucage and Carruthers, Tetrahedron Lett., 22:1859-1862 (1981).

Begemann, M. B. et al. Precise insertion and guided editing of higher plant genomes using Cpf1 CRISPR nucleases. bioRxiv, doi:10.1101/109983 (2017).

Boshart et al, A very Strong Enhancer is Located Upstream of an Immediate early Gene of Human Cytomegalovirus, Cell, 41:521-530 (1985).

(Continued)

*Primary Examiner* — Celine X Qian
*Assistant Examiner* — Catherine Konopka
(74) *Attorney, Agent, or Firm* — Meunier Carlin & Curfman LLC

(57) ABSTRACT

The present disclosure generally relates to genome editing systems and methods and compounds and compositions for use in Clustered Regularly Interspaced Short Palindromic Repeats (CRISPR) genome editing systems. Disclosed herein are modified nucleic acids that modulate the activity of genome editing.

3 Claims, 16 Drawing Sheets

Specification includes a Sequence Listing.

(56) References Cited

OTHER PUBLICATIONS

Bosley, K. S. et al. CRISPR germline engineering—the community speaks. Nature biotechnology 33, 478-486, doi: 10.1038/nbt.3227 (2015).
Dang, Y. et al. Optimizing sgRNA structure to improve CRISPR-Cas9 knockout efficiency. Genome biology 2015, 16, 280, doi:10.1186/s13059-015-0846-3 (2015).
Dong, D. et al. The crystal structure of Cpf1 in complex with CRISPR RNA. Nature 532, 522-526, doi:10.1038/nature17944 (2016).
Endo, A., Masafumi, M., Kaya, H. & Toki, S. Efficient targeted mutagenesis of rice and tobacco genomes using Cpf1 from Francisella novicida. Scientific reports 6, 38169, doi:10.1038/srep38169 (2016).
Fonfara, I., Richter, H., Bratovic, M., Le Rhun, A. & Charpentier, E. The CRISPR-associated DNA-cleaving enzyme Cpf1 also processes precursor CRISPR RNA. Nature 532, 517-521, doi:10.1038/nature17945 (2016).
Gao, P., Yang, H., Rajashankar, K. R., Huang, Z. & Patel, D. J. Type V CRISPR-Cas Cpf1 endonuclease employs a unique mechanism for crRNA-mediated target DNA recognition. Cell research 26, 901-913, doi:10.1038/cr.2016.88 (2016).
Henikoff and Henikoff (1989) Proc. Natl. Acad. Sci. USA 89:10915.
Hur, J. K. et al. Targeted mutagenesis in mice by electroporation of Cpf1 ribonucleoproteins. Nature biotechnology 34, 807-808, doi:10.1038/nbt.3596 (2016).
Juliano, R. L. The delivery of therapeutic oligonucleotides. Nucleic acids research 44, 6518-6548, doi:10.1093/nar/gkw236 (2016).
Karlin and Altschul (1993) Proc. Natl. Acad. Sci. USA 90:5873-5787.
Kim, D. et al. Genome-wide analysis reveals specificities of Cpf1 endonucleases in human cells. Nature biotechnology 34, 863-868, doi:10.1038/nbt.3609 (2016).
Kim, H. et al. CRISPR/Cpf1-mediated DNA-free plant genome editing. Nature communications 8, 14406, doi:10.1038/ncomms14406 (2017).
Kim, Y. et al. Generation of knockout mice by Cpf1-mediated gene targeting. Nature biotechnology 34, 808-810, doi:10.1038/nbt.3614 (2016).
Kleinstiver, B. P. et al. Genome-wide specificities of CRISPR-Cas Cpf1 nucleases in human cells. Nature biotechnology 34, 869-874, doi:10.1038/nbt.3620 (2016).
Latorre, A., Latorre, A. & Somoza, A. Modified RNAs in CRISPR/Cas9: An Old Trick Works Again. Angewandte Chemie 55, 3548-3550, doi:10.1002/anie.201512002 (2016).
Li, B. et al. Engineering CRISPR-Cpf1 crRNAs and mRNAs to maximize genome editing efficiency. Nature Biomedical Engineering 1, 0066 (2017).
Matteucci, et al., J. Am. Chem. Soc., 103:3185 (1981).
Nunez, J. K., Harrington, L. B. & Doudna, J. A. Chemical and Biophysical Modulation of Cas9 for Tunable Genome Engineering. ACS chemical biology 11, 681-688, doi:10.1021/acschembio.5b01019 (2016).
O'Hare, et al., Proc. Natl. Acad. Sci. USA., vol. 78(3), p. 1527-31, 1981.
Pawluk, A. et al. Naturally Occurring Off-Switches for CRISPR-Cas9. Cell 167, 1829-1838 e1829, doi:10.1016/j.cell.2016.11.017 (2016).
Rauch, B. J. et al. Inhibition of CRISPR-Cas9 with Bacteriophage Proteins. Cell 168, 150-158 e110, doi:10.1016/j.cell.2016.12.009 (2017).
Richter, F. et al. Switchable Cas9. Current opinion in biotechnology 48, 119-126, doi:10.1016/j.copbio.2017.03.025 (2017).
Stella, S., Alcon, P. & Montoya, G. Structure Of The Cpf1 Endonuclease R-Loop Complex After Target DNA Cleavage. bioRxiv, doi:10.1101/122648 (2017).
Swarts, D. C., van der Oost, J. & Jinek, M. Structural Basis for Guide RNA Processing and Seed-Dependent DNA Targeting by CRISPR-Cas12a. Molecular cell 66, 221-233 e224, doi: 10.1016/j.molcel.2017.03.016 (2017).
Takebe, et al., Mol. Cell. Biol., vol. 8(1), p. 466-472, 1988).
Tang, X. et al. A CRISPR-Cpf1 system for efficient genome editing and transcriptional repression in plants. Nature plants 3, 17018, doi:10.1038/nplants.2017.18 (2017).
Wang, M., Mao, Y., Lu, Y., Tao, X. & Zhu, J. K. Multiplex Gene Editing in Rice Using the CRISPR-Cpf1 System. Molecular plant, doi:10.1016/j.molp.2017.03.001 (2017).
Xu, R. et al. Generation of targeted mutant rice using a CRISPR-Cpf1 system. Plant biotechnology journal 15, 713-717, doi:10.1111/pbi.12669 (2017).
Yamano, T. et al. Crystal Structure of Cpf1 in Complex with Guide RNA and Target DNA. Cell 165, 949-962, doi:10.1016/j.cell.2016.04.003 (2016).
Yin, X. et al. CRISPR-Cas9 and CRISPR-Cpf1 mediated targeting of a stomatal developmental gene EPFL9 in rice. Plant cell reports 36, 745-757, doi:10.1007/s00299-017-2118-z (2017).
Zetsche, B. et al. Cpf1 is a single RNA-guided endonuclease of a class 2 CRISPR-Cas system. Cell 163, 759-771, doi:10.1016/j.cell.2015.09.038 (2015).
Zetsche, B. et al. Multiplex gene editing by CRISPR-Cpf1 using a single crRNA array. Nature biotechnology 35, 31-34, doi:10.1038/nbt.3737 (2017).
Zhang, Y. et al. CRISPR-Cpf1 correction of muscular dystrophy mutations in human cardiomyocytes and mice. Science Advances 3, doi:10.1126/sciadv.1602814 (2017).
International Preliminary Report on Patentability issued for Application No. PCT/US2017/041133, dated Jan. 17, 2019.
Makarova et al., 2015. An updated evolutionary classification of CRISPR-Cas systems. Nat Rev Microbial. 13(11): 722-736 (Year: 2015).
Leenay et al., Apr. 2016. Identifying and Visualizing Functional PAM Diversity across CRISPR-Cas Systems. Mol Cell., 62, 137-147 (Year: 2016).
Cong et al., 2013. Multiplex Genome Engineering Using CRISPR/Cas Systems. Science 339 p. 819-823 (Year: 2013).
Jakociunas et al., 2015. Multiplex metabolic pathway engineering using CRISPR/Cas9 in *Saccharomyces cerevisiae*. Metabolic Engineering 28, 213-222 (Year: 2015).
Chang et al., 2012. Synthetic RNA switches as a tool for temporal and spatial control over gene expression. Current Opinion in Biotechnology 23:679-688 (Year: 2012).
Zhang and Seelig 2011. Dynamic DNA nanotechnology using strand displacement reactions. Nat. Chem. vol. 3, 103-113 (Year: 2011).
Braasch et al., 2003. RNA Interference in Mammalian Cells by Chemically-Modified RNA. Biochemistry 42, 7967-7975 (Year: 2003).
Rahdar et al., 2015. Synthetic CRISPR RNA-Cas9-guided genome editing in human cells. PNAS, E7110-E7117 (Year: 2015).
Zetsche et al., 2016. Cpf1 Is a Single RNA-Guided Endonuclease of a Class 2 CRISPR-Cas System. Cell 163, 759-771 (Year: 2016.
Gilbert, Luke A., et al. "CRISPR-mediated modular RNA-guided regulation of transcription in eukaryotes." Cell 154.2 (2013): 442-451.
Hua, Yimin, et al. "Motor neuron cell-nonautonomous rescue of spinal muscular atrophy phenotypes in mild and severe transgenic mouse models." Genes & development (2015). vol. 29, No. 3: 288-297.
Rahdar, Meghdad, et al. "Synthetic CRISPR RNA-Cas9-guided genome editing in human cells." Proceedings of the National Academy of Sciences 112.51 (2015): E7110-E7117.
Zhang, Yan, et al. "DNase H activity of Neisseria meningitidis Cas9." Molecular cell 60.2 (2015): 242-255.
International Search Report and Written Opinion of the U.S. International Searching Authority. Application No. PCT/US2017/041133. Mailed Sep. 25, 2017. 17 pages.

* cited by examiner ps42DNA
-AAVS1
1,000
800
600
400
200
AsCpf1 crRNA and mRNA treated HEK293T cells, AAVS locus
-
+ at 0h
+ at 1h
+ at 3h
+ at 5h
+ at 10h
41±5
ND
ND
ND
18±9
34±1 ps42DNA
-FANCF
1,000
800
600
400
200
AsCpf1 crRNA and mRNA treated HEK293T cells, FANCF locus
-
+ at 0h
+ at 1h
+ at 3h
+ at 5h
+ at 10h
39±2
ND
ND
ND
6±0.1
23±1

MODIFIED NUCLEIC ACIDS, HYBRID GUIDE RNAS, AND USES THEREOF

CROSS REFERENCE TO RELATED APPLICATIONS

This application claims the benefit of U.S. Provisional Patent Application Ser. No. 62/359,880, filed Jul. 8, 2016 and U.S. Provisional Patent Application Ser. No. 62/480,716 filed Apr. 3, 2017, each of which are expressly incorporated herein by reference.

STATEMENT REGARDING FEDERALLY SPONSORED RESEARCH

This invention was made with Government Support under Grant No. R01HL136652 awarded by the National Heart, Lung, and Blood Institute. The Government has certain rights to the invention.

REFERENCE TO SEQUENCE LISTING

A Sequence Listing conforming to the rules of WIPO Standard ST.26 is hereby incorporated by reference. Said Sequence Listing has been filed as an electronic document via PatentCenter in ASCII format encoded as XML. The electronic document, created on Feb. 22, 2024, is entitled “10336-274US2-ST26.xml”, and is 60,111 bytes in size.

FIELD

The present disclosure generally relates to compounds and methods for use in genome editing systems.

BACKGROUND

Cpf1 (CRISPR from *Prevotella* and *Francisella* 1) is one of the CRISPR associated effector endonucleases, which induces double stranded DNA breaks under the guidance of a single CRISPR RNA (crRNA). The wild-type crRNA of CRISPR-Cpf1 system comprises a 5'-handle engaging Cpf1 recognition and a guide segment interacting with targeted DNA sequences through complimentary bindings. Based on its unique gene editing properties, the CRISPR-Cpf1 system has recently been applied in diverse eukaryotic species including plants and animals to achieve targeted genome editing.

Although the CRISPR system offers a powerful platform for genome editing, a number of challenges exist for its therapeutic applications including gene editing efficiency and potential side effects. Previously, extensive efforts have been made to improve gene editing efficiency. Meanwhile, researchers have also investigated diverse approaches to modulate the activity of the CRISPR system. Due to the potential for severe side effects in these genome editing systems, it is essential to prepare an effective and fast mechanism to switch off its function. Recently, anti-CRISPR proteins from bacteriophage or bacteria were discovered to inhibit the function of *Listeria monocytogenes* or *Neisseria meningitidis* CRISPR-Cas9. In addition, multiple strategies such as chemical-, temperature- and light-triggered approaches were developed to regulate the CRISPR-Cas9 system. However, no method is currently available to effectively regulate the CRISPR-Cpf1 system including upregulation, downregulation, and complete inactivation.

The compounds, compositions, and methods disclosed herein address these and other needs.

SUMMARY

The inventors have designed and synthesized a novel array of nucleic acid molecules for use as adjustable switches to upregulate, downregulate, and completely inactivate the cleavage activity of Cpf1 in the CRISPR genome editing system. In some embodiments, these nucleic acid molecules comprise chemically modified nucleotides and/or chimeric DNA/RNA guide molecules.

In one aspect, disclosed herein is an isolated nucleic acid comprising at least one chemically modified nucleotide, wherein the nucleic acid is complementary to a guide RNA of a CRISPR genome editing system.

In one aspect, disclosed herein is a method for inhibiting a CRISPR genome editing system in a cell comprising:

- contacting the cell with a CRISPR genome editing system, wherein the system comprises a guide RNA and a nuclease;
- contacting the cell with a chemically modified nucleic acid comprising at least one chemically modified nucleotide;
- wherein the nucleic acid is complementary to the guide RNA; and
- wherein the chemically modified nucleic acid inhibits the activity of the nuclease of the CRISPR genome editing system.

In another aspect, disclosed herein is a method for increasing the nuclease activity of a CRISPR genome editing system in a cell comprising:

- contacting the cell with a CRISPR genome editing system, wherein the system comprises a guide RNA and a nuclease;
- contacting the cell with a chemically modified nucleic acid comprising at least one chemically modified nucleotide;
- wherein the nucleic acid is complementary to the guide RNA; and
- wherein the chemically modified nucleic acid increases the activity of the nuclease of the CRISPR genome editing system.

In some embodiments, the at least one chemically modified nucleotide comprises a chemically modified nucleobase, a chemically modified ribose, a chemically modified phosphodiester linkage, or a combination thereof. In some embodiments, the at least one chemically modified nucleotide is a chemically modified phosphodiester linkage. In some embodiments, the chemically modified phosphodiester linkage is phosphorothioate (PS).

In some embodiments, all the nucleotides comprise chemically modified phosphodiester linkages. In some embodiments, the chemically modified phosphodiester linkages are phosphorothioate (PS).

In some embodiments, the nucleic acid inhibits a nuclease activity of the CRISPR genome editing system. In some embodiments, the at least one chemically modified nucleotide is a chemically modified ribose. In some embodiments, the chemically modified ribose is 2'-O-methyl (2'-O-Me) or 2'-fluoro (2'-F). In some embodiments, the chemically modified ribose is 2'-O-methyl (2'-O-Me). In some embodiments, the chemically modified ribose is 2'-fluoro (2'-F).

In some embodiments, the nucleic acid increases a nuclease activity of the CRISPR genome editing system.

In some embodiments, the complementary region between the nucleic acid and the guide RNA comprises at least 5 nucleotides. In some embodiments, the complementary region between the nucleic acid and the guide RNA comprises at least 10 nucleotides. In some embodiments, the nucleic acid is about 10 to about 43 nucleotides in length.

In some embodiments, the nucleic acid is RNA. In some embodiments, the nucleic acid is DNA. In some embodiments, the nuclease activity is from a Cpf1 protein.

In one aspect, disclosed herein is a chimeric guide nucleic acid comprising at least one RNA nucleotide and at least one DNA nucleotide, wherein the chimeric guide nucleic acid inhibits a nuclease activity of a CRISPR genome editing system.

In a further aspect, disclosed herein is a method for inhibiting a CRISPR genome editing system in a cell comprising:

- contacting the cell with a CRISPR genome editing system, wherein the system comprises a guide RNA and a nuclease;
- contacting the cell with a chimeric guide nucleic acid comprising at least one RNA nucleotide and at least one DNA nucleotide; and
- wherein the chimeric guide nucleic acid inhibits the activity of the nuclease of the CRISPR genome editing system.

In some embodiments, the nucleic acid is comprised of at least 5% DNA nucleotides. In some embodiments, the nucleic acid is comprised of at least 10% DNA nucleotides. In some embodiments, the nucleic acid is comprised of at least 30% DNA nucleotides. In some embodiments, the nucleic acid is comprised of at least 50% DNA nucleotides.

In some embodiments, the nuclease activity is from a Cpf1 protein. In some embodiments, the nucleic acid is about 10 to about 43 nucleotides in length.

In some embodiments, the nucleic acid comprises at least one chemically modified nucleotide. In some embodiments, the at least one chemically modified nucleotide comprises a chemically modified nucleobase, a chemically modified ribose, a chemically modified phosphodiester linkage, or a combination thereof.

BRIEF DESCRIPTION OF THE DRAWINGS

The accompanying figures, which are incorporated in and constitute a part of this specification, illustrate several aspects described below.

FIG. 1A, Schematic illustration of crRNA chimeras. Wild-type crRNA consists of a handle (pseudo-knot structure) and a guide segment. crRNA chimeras were synthesized by substituting of ribonucleotides (gray) with corresponding deoxynucleotides (black). FIG. 1B, Relative gene cutting efficiency of crRNA chimeras in the presence of AsCpf1 plasmid for the DNMT1 locus in HEK293T cells. FIG. 1C, Schematic illustration of DNA-crRNA duplexes. Duplexes were formed by hybridization of different lengths of unmodified (crRNA1I to crRNA14) or PS-modified (crRNA15, 16, 17) DNA oligonucleotides with various regions of the crRNA. FIG. 1E, Relative Gene cutting efficiency of DNA-crRNA duplexes in the presence of AsCpf1 plasmid for the DNMT1 locus in HEK293T cells. FIG. 1E, Schematic illustration of RNA-crRNA duplexes. Duplexes were formed by hybridization of unmodified (crRNA18, 19, 20), 2'-fluoro modified (crRNA21, 22) or 2'-O-Methyl modified (crRNA23, 24, 25) RNA oligonucleotides with of the crRNA. FIG. 1F, Relative Gene cutting efficiency of RNA-crRNA duplexes in the presence of AsCpf1 plasmid for the DNMT1 locus in HEK293T cells ( P<0.01, crRNA24 versus crRNA; two-tailed t-test). FIG. 1**gG Relative Gene cutting efficiency of PS-DNA-crRNA duplexes in the presence of AsCpf1 mRNA for the DNMT1 locus in HEK293T cells. In all cases, relative gene cutting (%) was determined by the T7E1 cleavage assay, and normalized to that of the wild-type crRNA group. All data are expressed as the mean±s.d. from three biological replicates. ND, not detectable.

FIGS. 2A, 2B, Time- (2A) and dose- (2B) dependent effects of ps42DNA on AsCpf1-mediated DNMT1 gene cutting in HEK293T cells. FIGS. 2C, 2D, Time-dependent effects of ps42DNA-AAVS1 on AsCpf1-mediated gene cutting at the AAVS1 locus (2C), and ps42DNA-FANCF on AsCpf1-mediated gene cutting at the FANCF locus (2D). FIG. 2E, Time-dependent effects of ps42DNA on AsCpf1-mediated DNMT1 gene cleavage in Hep3B cells. FIG. 2F, Time-dependent effects of Lbps42DNA on LbCpf1-mediated gene cutting at the DNMT1 locus in HEK293T cells. Relative gene cutting was determined by the T7E1 cleavage assay, normalized to that of the treatment with wild-type crRNA and AsCpf1 mRNA, and plotted versus time or dose. The corresponding gel images were shown in FIG. 4.

FIGS. 4A, 4B, Time- (4A) and dose- (4B) dependent effects of ps42DNA on AsCpf1-mediated DNMT1 gene cutting in HEK293T cells. FIGS. 4C, 4D, Time-dependent effects of ps42DNA-AAVS1 on AsCpf1-mediated gene cutting at the AAVS1 locus (4C), and ps42DNA-FANCF on AsCpf1-mediated gene cutting at the FANCF locus (4D). FIG. 4E, Time-dependent effects of ps42DNA on AsCpf1-mediated DNMT1 gene cleavage in Hep3B cells. FIG. 4F, Time-dependent effects of Lbps42DNA on LbCpf1-mediated gene cutting at the DNMT1 locus in HEK293T cells. Indels were determined by the T7E1 cleavage assay, normalized to that of the treatment with wild-type crRNA and AsCpf1 mRNA, and plotted versus time or dose. The lane marked with "x" is excluded for calculation of gene cutting efficiency. The asterisk denotes the non-specific band. The grey and black arrows denote the intact and cleaved product, respectively.

FIG. 5A, Schematic illustration of fluorescently labeled crRNA and variants. The light grey letters denote the unmodified RNA base. The black letter denotes unmodified DNA base. The dark grey letters denote PS-linkage modified DNA (see ps42DNA-Cy5crRNA). FIG. 5B, Gene cutting efficiency of Cy5crRNA (left) and crRNA-Cy3uDNA (right) on DNMT1 locus in HEK293T cells. FIG. 5C, Effects of Cy3uDNA on AsCpf1-mediated DNMT1 gene cleavage in HEK293T cells. FIG. 5D, Gene cutting efficiency of crRNA-Cy3uDNA-AAVS1 on AAVS1 locus (left) and crRNA-Cy3uDNA-FANCF on FANCF locus (right) in HEK293T cells. FIG. 5E, Gene cutting efficiency of crRNA-intCy3uDNA and crRNA-3'Cy3uDNA on DNMT1 locus in HEK293T cells. Indels were determined by the T7E1 cleavage assay, normalized to that of the treatment with wild-type crRNA and AsCpf1 mRNA. The grey and black arrows denote the intact and cleaved product, respectively.

DETAILED DESCRIPTION

Figure 1A:
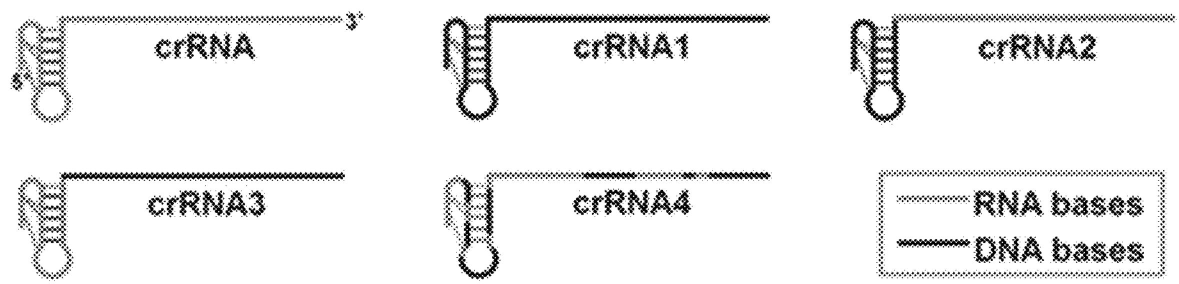
FIGS. 1A-1G. Gene cutting efficiency of crRNA variants in human cells.

The inventors have designed and synthesized a novel array of nucleic acid molecules for use as adjustable switches to upregulate, downregulate, and completely inactivate the cleavage activity of Cpf1 in the CRISPR genome editing system. In some embodiments, these nucleic acid molecules comprise chemically modified nucleotides and/or chimeric DNA/RNA guide molecules.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.,* 22:1859-1862 (1981), or by the triester method according to Matteucci, et al., *J. Am. Chem. Soc.,* 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and HI promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N. Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci*. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

The terms "guide RNA", "gRNA", "CRISPR RNA", or "crRNA" are used interchangeably throughout the specification and refers to the RNA associated with one of the CRISPR gene editing systems. This crRNA (or guide RNA) consists of a 5'-handle and a guide segment. Cpf1 protein interacts with the pseudoknot structure formed by the 5'-handle of crRNA (or guide RNA). The guide segment possesses complementary binding with the target DNA sequences.

The term "about" as used herein when referring to a measurable value such as an amount, a percentage, and the like, is meant to encompass variations of +20%, +10%, +5%, or +1% from the measurable value.

Modified Nucleic Acids, Hybrid Guide RNAs, and Methods of Use

In one aspect, disclosed herein is an isolated nucleic acid comprising at least one chemically modified nucleotide, wherein the nucleic acid is complementary to a guide RNA of a CRISPR genome editing system.

In some embodiments, the at least one chemically modified nucleotide comprises a chemically modified nucleobase, a chemically modified ribose, a chemically modified phosphodiester linkage, or a combination thereof. In some embodiments, the at least one chemically modified nucleotide is a chemically modified phosphodiester linkage. In some embodiments, the chemically modified phosphodiester linkage is phosphorothioate (PS).

In some embodiments, all the nucleotides comprise chemically modified phosphodiester linkages. In some embodiments, the chemically modified phosphodiester linkages are phosphorothioate (PS).

In some embodiments, the nucleic acid inhibits a nuclease activity of the CRISPR genome editing system. In some embodiments, the at least one chemically modified nucleotide is a chemically modified ribose. In some embodiments, the chemically modified ribose is 2'-O-methyl (2'-O-Me) or 2'-fluoro (2'-F). In some embodiments, the chemically modified ribose is 2'-O-methyl (2'-O-Me). In some embodiments, the chemically modified ribose is 2'-fluoro (2'-F).

In some embodiments, the nucleic acid increases a nuclease activity of the CRISPR genome editing system.

In some embodiments, the complementary region between the nucleic acid and the guide RNA comprises at least 10 nucleotides. In some embodiments, the nucleic acid is about 10 to about 43 nucleotides in length.

In some embodiments, the nucleic acid is RNA. In some embodiments, the nucleic acid is DNA. In some embodiments, the nuclease activity is from a Cpf1 protein.

In one aspect, disclosed herein is a method for inhibiting a CRISPR genome editing system in a cell comprising:

- contacting the cell with a CRISPR genome editing system, wherein the system comprises a guide RNA and a nuclease;
- contacting the cell with a chemically modified nucleic acid comprising at least one chemically modified nucleotide;

wherein the nucleic acid is complementary to the guide RNA; and wherein the chemically modified nucleic acid inhibits the activity of the nuclease of the CRISPR genome editing system.

In some embodiments, the at least one chemically modified nucleotide comprises a chemically modified nucleobase, a chemically modified ribose, a chemically modified phosphodiester linkage, or a combination thereof. In some embodiments, the at least one chemically modified nucleotide is a chemically modified phosphodiester linkage. In some embodiments, the chemically modified phosphodiester linkage is phosphorothioate (PS).

In some embodiments, all the nucleotides comprise chemically modified phosphodiester linkages. In some embodiments, the chemically modified phosphodiester linkages are phosphorothioate (PS).

In some embodiments, the complementary region between the nucleic acid and the guide RNA comprises at least 10 nucleotides. In some embodiments, the nucleic acid is about 10 to about 43 nucleotides in length.

In some embodiments, the nucleic acid is RNA. In some embodiments, the nucleic acid is DNA. In some embodiments, the nuclease activity is from a Cpf1 protein.

In another aspect, disclosed herein is a method for increasing the nuclease activity of a CRISPR genome editing system in a cell comprising:

contacting the cell with a CRISPR genome editing system, wherein the system comprises a guide RNA and a nuclease;

contacting the cell with a chemically modified nucleic acid comprising at least one chemically modified nucleotide;

wherein the nucleic acid is complementary to the guide RNA; and wherein the chemically modified nucleic acid increases the activity of the nuclease of the CRISPR genome editing system.

In some embodiments, the at least one chemically modified nucleotide comprises a chemically modified nucleobase, a chemically modified ribose, a chemically modified phosphodiester linkage, or a combination thereof. In some embodiments, the at least one chemically modified nucleotide is a chemically modified ribose. In some embodiments, the chemically modified ribose is 2'-O-methyl (2'-O-Me) or 2'-fluoro (2'-F). In some embodiments, the chemically modified ribose is 2'-O-methyl (2'-O-Me). In some embodiments, the chemically modified ribose is 2'-fluoro (2'-F).

In some embodiments, the complementary region between the nucleic acid and the guide RNA comprises at least 10 nucleotides. In some embodiments, the nucleic acid is about 10 to about 43 nucleotides in length.

In some embodiments, the nucleic acid is RNA. In some embodiments, the nucleic acid is DNA. In some embodiments, the nuclease activity is from a Cpf1 protein.

In yet a further aspect, disclosed herein is a chimeric guide nucleic acid comprising at least one RNA nucleotide and at least one DNA nucleotide, wherein the chimeric guide nucleic acid inhibits a nuclease activity of a CRISPR genome editing system.

In some embodiments, the nucleic acid is comprised of at least 5% DNA nucleotides. In some embodiments, the nucleic acid is comprised of at least 10% DNA nucleotides. In some embodiments, the nucleic acid is comprised of at least 30% DNA nucleotides. In some embodiments, the nucleic acid is comprised of at least 50% DNA nucleotides.

In some embodiments, the nuclease activity is from a Cpf1 protein. In some embodiments, the nucleic acid is about 10 to about 43 nucleotides in length.

In some embodiments, the nucleic acid comprises at least one chemically modified nucleotide. In some embodiments, the at least one chemically modified nucleotide comprises a chemically modified nucleobase, a chemically modified ribose, a chemically modified phosphodiester linkage, or a combination thereof.

In one aspect, disclosed herein is a method for inhibiting a CRISPR genome editing system in a cell comprising:

contacting the cell with a CRISPR genome editing system, wherein the system comprises a guide RNA and a nuclease;

contacting the cell with a chimeric guide nucleic acid comprising at least one RNA nucleotide and at least one DNA nucleotide; and wherein the chimeric guide nucleic acid inhibits the activity of the nuclease of the CRISPR genome editing system.

In some embodiments, the nucleic acid is comprised of at least 5% DNA nucleotides. In some embodiments, the nucleic acid is comprised of at least 10% DNA nucleotides. In some embodiments, the nucleic acid is comprised of at least 30% DNA nucleotides. In some embodiments, the nucleic acid is comprised of at least 50% DNA nucleotides.

In some embodiments, the nuclease activity is from a Cpf1 protein. In some embodiments, the nucleic acid is about 10 to about 43 nucleotides in length.

In some embodiments, the nucleic acid comprises at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the CRISPR genome editing system comprises:

a) a guide RNA that hybridizes with a target sequence of a DNA molecule in a eukaryotic cell that contains the DNA molecule, and b) a DNA vector comprising a regulatory element operable in a eukaryotic cell operably linked to a nucleotide sequence encoding a Cpf1 protein; an mRNA encoding a Cpf1 protein; or a Cpf1 protein.

In one aspect, disclosed herein is a method for inhibiting a CRISPR genome editing system in a cell comprising:

contacting the cell with a chemically modified nucleic acid comprising at least one chemically modified nucleotide;

wherein the nucleic acid is complementary to the guide RNA; and wherein the chemically modified nucleic acid inhibits the activity of the nuclease of the CRISPR genome editing system.

In another aspect, disclosed herein is a method for increasing the nuclease activity of a CRISPR genome editing system in a cell comprising:

contacting the cell with a chemically modified nucleic acid comprising at least one chemically modified nucleotide;

wherein the nucleic acid is complementary to the guide RNA; and wherein the chemically modified nucleic acid increases the activity of the nuclease of the CRISPR genome editing system.

In one aspect, disclosed herein is an isolated deoxyribonucleic acid, wherein the deoxyribonucleic acid is complementary to a guide RNA of a CRISPR genome editing system, wherein the deoxyribonucleic acid inhibits a nuclease activity of the CRISPR genome editing system.

The class II CRISPR system bearing single protein effector, such as CRISPR-Cas9 and CRISPR-Cpf1, has been shown to induce precise genome cleavage in human cells. Given that guide RNA (gRNA) plays a critical role in capturing endonucleases and subsequent targeting to specific genomic regions, a series of short or full-length oligodeoxynucleotides (ODNs) that are complementary with guide DNA, and forged DNA-RNA heteroduplexes via base-pairing between ODNs and guide RNA were designed and disclosed herein.

In some embodiments, disclosed herein is a nucleic acid composition comprising an oligonucleotide selected from the group consisting of any of the oligonucleotides listed in Table 1. In some embodiments, disclosed herein is an isolated nucleic acid selected from the group consisting of any of oligodeoxynucleotides (ODNs) listed in Table 1. Also disclosed herein is an isolated hybrid guide RNA composition as described herein and a method of inducing genome cleavage as described herein. In some embodiments, disclosed herein a nucleic acid (hybrid guide RNA) composition selected from the group consisting of any of the oligonucleotides shown FIG. 1. Also provided are methods for eukaryotic genome editing utilizing nucleic acid molecules in complex with a class II CRISPR endonuclease, including Cpf1 or Cas9, as described herein.

In some embodiments, the nuclease activity is from a Cpf1 protein. In some embodiments, the nuclease activity is from a Cas9 protein.

In some embodiments, the nucleic acid molecule (for example, DNA) is complementary to the entire guide RNA molecule. The complementary molecule forms a double stranded DNA/RNA hybrid guide molecule with the guide RNA (hybrid guide RNA). In some embodiments, the nucleic acid molecule is complementary over a portion of the guide RNA molecule. In some embodiments, the nucleic acid molecule is complementary to the guide portion of the guide RNA molecule. In some embodiments, the nucleic acid molecule is complementary to the handle portion of the guide RNA molecule. In some embodiments, the nucleic acid molecule is complementary over at least 10 nucleotides (for example at least 10, at least 15, at least 20, at least 25, at least 30, at least 35, at least 40) of the guide RNA molecule. In some embodiments, the nucleic acid molecule is complementary over about 10 to about 20 nucleotides, over about 15 to about 30 nucleotides, over about 20 to about 35 nucleotides of the guide RNA molecule.

Chemically Modified Nucleotides

In some embodiments, the nucleic acids disclosed herein comprise at least one chemically modified nucleotide. In some embodiments, the at least one chemically modified nucleotide comprises a chemically modified nucleobase, a chemically modified ribose, a chemically modified phosphodiester linkage, or a combination thereof.

In some embodiments, the mRNA encoding a Cpf1 protein comprises at least one chemically modified nucleotide selected from a chemically modified nucleobase, a chemically modified ribose, a chemically modified phosphodiester linkage, or a combination thereof.

In some embodiments, the guide RNA comprises at least one chemically modified nucleotide selected from a chemically modified nucleobase, a chemically modified ribose, a chemically modified phosphodiester linkage, or a combination thereof.

Chemically Modified Nucleobases

In one embodiment, the at least one chemically modified nucleotide is a chemically modified nucleobase.

In one embodiment, the chemically modified nucleobase is selected from 5-formylcytidine (5fC), 5-methylcytidine (5meC), 5-methoxycytidine (5moC), 5-hydroxycytidine (5hoC), 5-hydroxymethylcytidine (5hmC), 5-formyluridine (5fU), 5-methyluridine (5-meU), 5-methoxyuridine (5moU), 5-carboxymethylesteruridine (5camU), pseudouridine (Ψ), N1-methylpseudouridine ($me^1Ψ$), $N^6$-methyladenosine ($me^6A$), or thienoguanosine ($^{th}G$).

In some embodiments, the chemically modified nucleobase is selected from 5-methoxyuridine (5moU), pseudouridine (Ψ), and $N^1$-methylpseudouridine ($me^1Ψ$). In some embodiments, the chemically modified nucleobase is 5-methoxyuridine (5moU). In some embodiments, the chemically modified nucleobase is pseudouridine (Ψ). In some embodiments, the chemically modified nucleobase is $N^1$-methylpseudouridine ($me^1Ψ$).

In some embodiments, the at least one chemically modified nucleobase comprises N1-methylpseudouridine ($me^1Ψ$) and 5-methylcytidine (5meC). In some embodiments, the at least one chemically modified nucleobase comprises pseudouridine (Ψ) and 5-methylcytidine (5meC). In some embodiments, the at least one chemically modified nucleobase comprises 5-methyluridine (5-meU) and 5-methoxycytidine (5moC). In some embodiments, the at least one chemically modified nucleobase comprises 5-methyluridine (5-meU) and 5-hydroxymethylcytidine (5hmC).

The structures of these modified nucleobases are shown below:

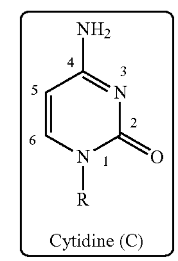

Cytidine (C)

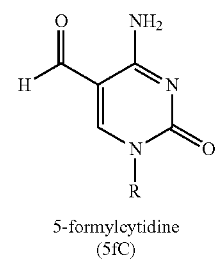

5-formylcytidine (5fC)

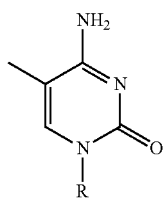

5-methylcytidine (5meC)

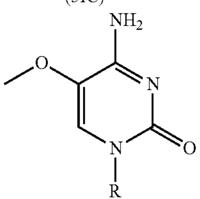

5-methoxycytidine (5moC)

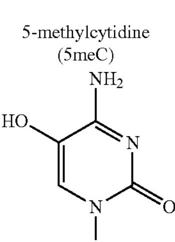

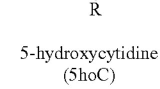

5-hydroxycytidine (5hoC)

5-hydroxymethyl-cytidine (5hmC)

-continued

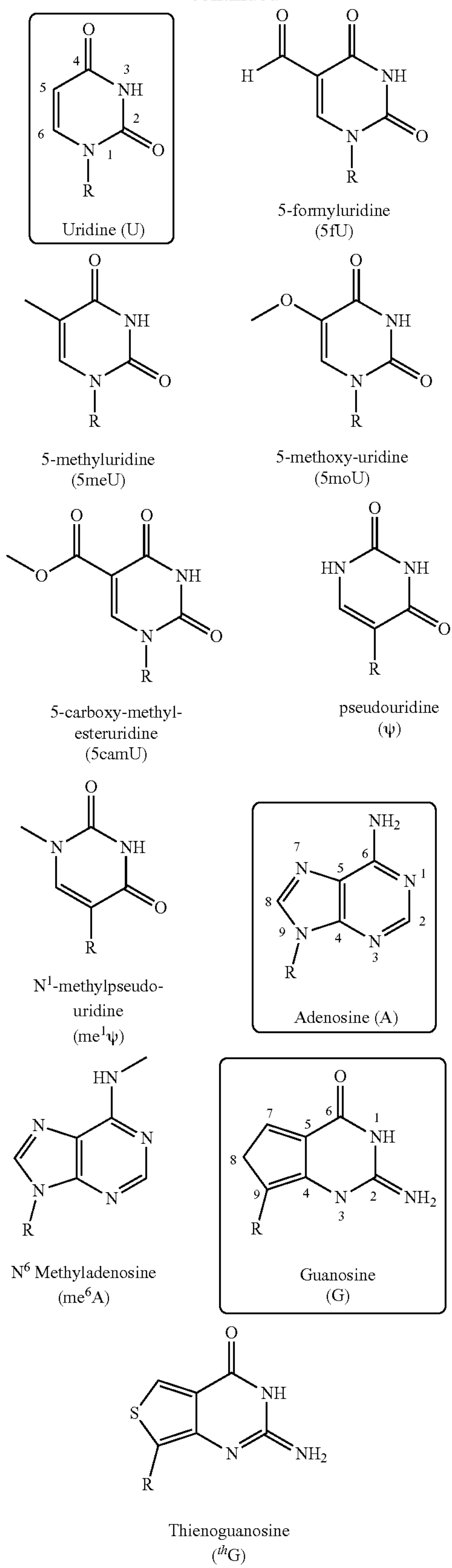

In addition to a chemically modified nucleobase in the complementary RNAs that form hybrid guide RNAs and/or in the novel chimeric nucleic acids disclosed herein, a chemically modified nucleobase can also be used in the mRNA encoding a Cpf1 protein and/or the guide RNA of the CRISPR genome editing systems. In some embodiments, the mRNA encoding a Cpf1 protein comprises a chemically modified nucleobase. In some embodiments, the guide RNA comprises a chemically modified nucleobase.

Chemically Modified Ribose Moieties

In one embodiment, the at least one chemically modified nucleotide is a chemically modified ribose.

5 In one embodiment, the chemically modified ribose is selected from 2'-O-methyl (2'-O-Me), 2'-Fluoro (2'-F), 2'-deoxy-2'-fluoro-beta-D-arabino-nucleic acid (2'F-ANA), 4'-S, 4'-SFANA, 2'-azido, UNA, 2'-O-methoxy-ethyl (2'-O-ME), 2'-O-Allyl, 2'-O-Ethylamine, 2'-O-Cyanoethyl, Locked nucleic acid (LAN), Methylene-cLAN, N-MeO-amino BNA, or N-MeO-aminooxy BNA. In one embodiment, the chemically modified ribose is selected from 2'-O-methyl (2'-O-Me) or 2'-Fluoro (2'-F). In one embodiment, the chemically modified ribose is 2'-O-methyl 10 (2'-O-Me). In one embodiment, the chemically modified ribose is 2'-Fluoro (2'-F).

The structures of these modified riboses are shown below:

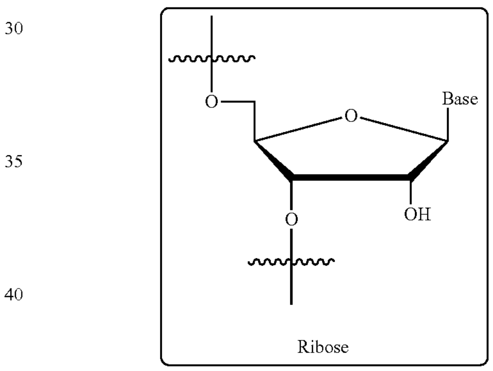

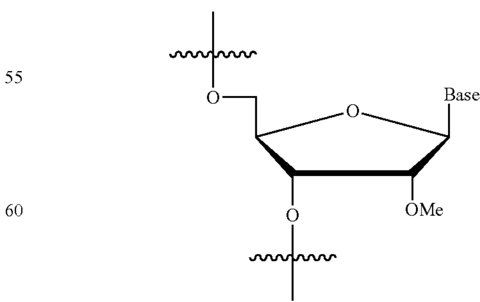

2′-O-methyl
(2′-O-Me)

-continued
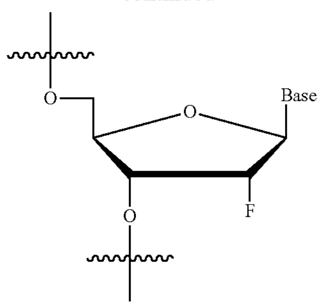
2′-Fluoro
(2′-F)
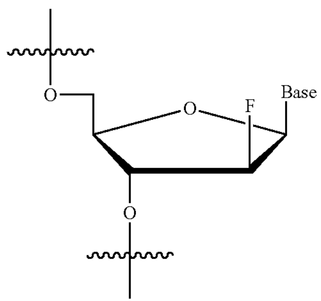
2′-deoxy-2′-fluoro-beta-D-arabino-nucleic acid
(2′F-ANA)
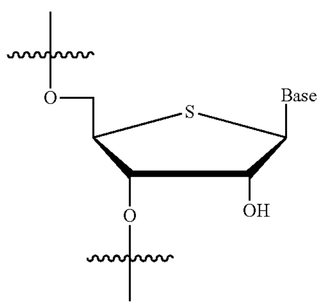
4′-S
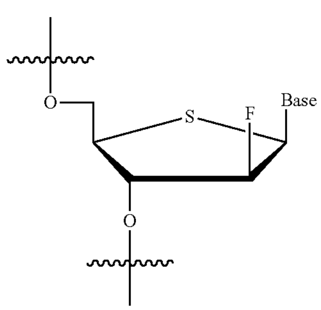
4′-SFANA
-continued
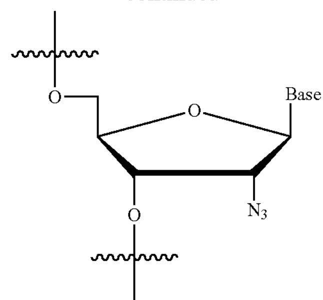
2′-azido
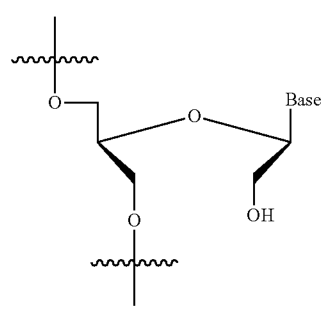
UNA
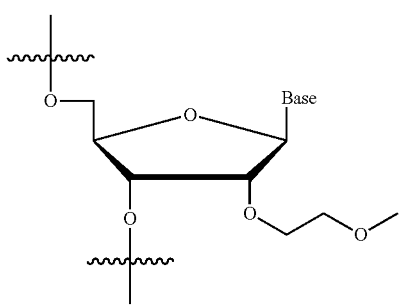
2′-O-methoxy-ethyl (2′-O-ME)
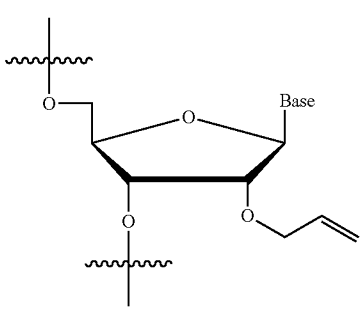
2′-O-Allyl -continued

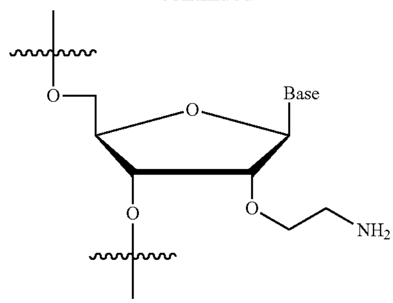

2'-O-Ethylamine

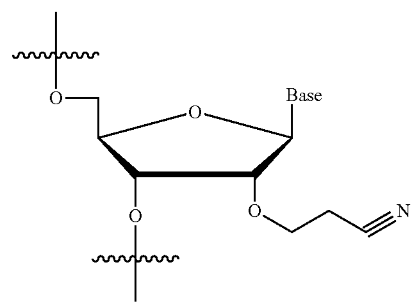

2'-O-Cyanoethyl

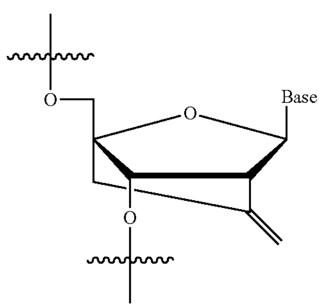

Methylene-cLAN

-continued

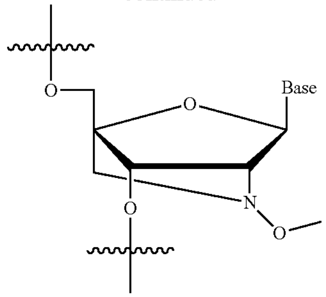

N-MeO-amino BNA

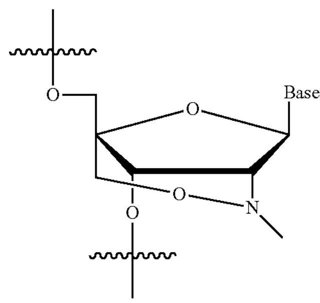

N-MeO-aminooxy BNA

Locked nucleic acid (LAN)

In addition to a chemically modified ribose in the complementary RNAs that form hybrid guide RNAs and/or in the novel chimeric nucleic acids disclosed herein, a chemically modified ribose can also be used in the mRNA encoding a Cpf1 protein and/or the guide RNA of the CRISPR genome editing systems. In some embodiments, the mRNA encoding a Cpf1 protein comprises a chemically modified ribose. In some embodiments, the guide RNA comprises a chemically modified ribose.

Chemically Modified Phosphodiester Backbone

In one embodiment, the at least one chemically modified nucleotide is a chemically modified phosphodiester linkage.

In one embodiment, the chemically modified phosphodiester linkage is selected from phosphorothioate (PS), boranophosphate, phosphodithioate (PS2), 3',5'-amide, N3'-phosphoramidate (NP), Phosphodiester (PO), or 2',5'-phosphodiester (2',5'-PO). In one embodiment, the chemically modified phosphodiester linkage is phosphorothioate.

The structures of these modified phosphodiester linkages are shown below:
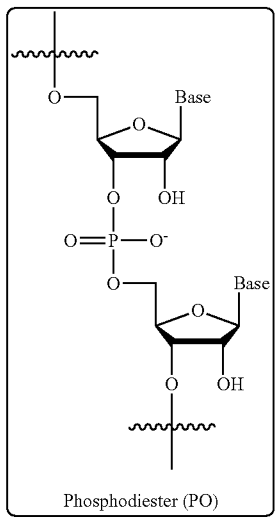
Phosphodiester (PO)
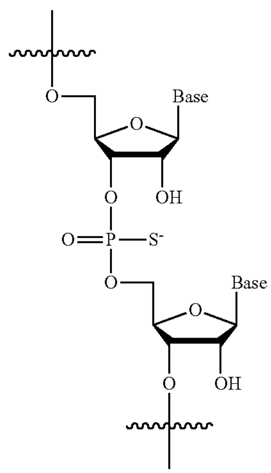
Phosphorothioate (PS)
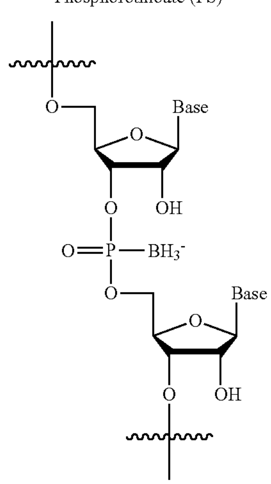
Boranophosphate
-continued
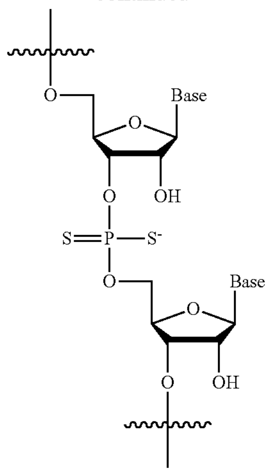
Phosphodithioate (PS2)
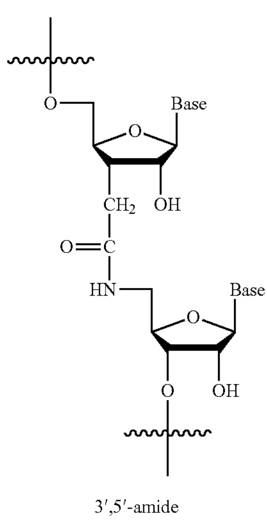
3′,5′-amide
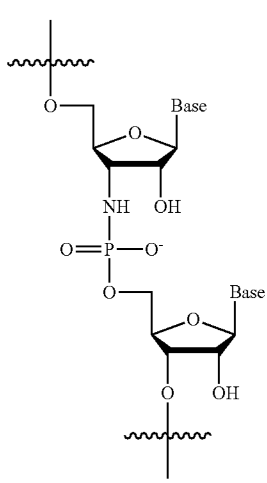
N3′-phosphoroamidate (NP)

-continued

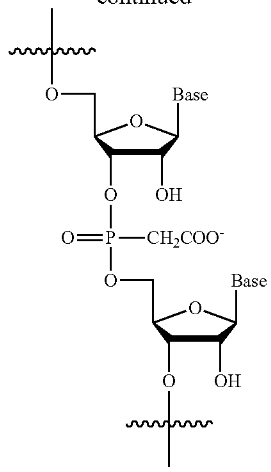

Phosphodiester (PO)

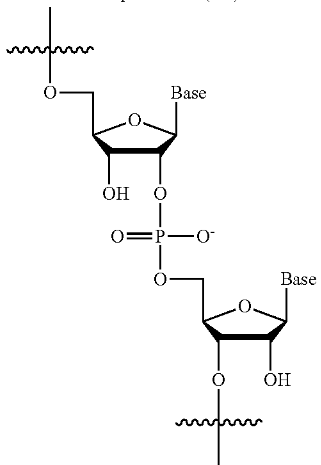

2′,5′-phosphodiester (2′,5′-PO)

In addition to a chemically modified phosphodiester linkage in the complementary RNAs that form hybrid guide RNAs and/or in the novel chimeric nucleic acids disclosed herein, a chemically modified phosphodiester linkage can also be used in the mRNA encoding a Cpf1 protein and/or the guide RNA of the CRISPR genome editing systems. In some embodiments, the mRNA encoding a Cpf1 protein comprises a chemically modified phosphodiester linkage. In some embodiments, the guide RNA comprises a chemically modified phosphodiester linkage.

Cpf1 Protein

In one embodiment, the Cpf1 protein is encoded by SEQ ID NO:1. This sequence can be codon optimized, can differ due to the degeneracy of the genetic code, can be similar, or share substantial identity, to SEQ ID NO:1, but still retain nuclease activity.

```
AsCpf1 sequence (SEQ ID NO: 1)
                                            (SEQ ID NO: 1)
ATGGCCCCAAAGAAGAAGCGGAAGGTCGGTATCCACGGAGTCCCAGCAGC

CACACAGTTCGAGGGCTTTACCAACCTGTATCAGGTGAGCAAGACACTGC

GGTTTGAGCTGATCCCACAGGGCAAGACCCTGAAGCACATCCAGGAGCAG

GGCTTCATCGAGGAGGACAAGGCCCGCAATGATCACTACAAGGAGCTGAA
```

-continued

```
GCCCATCATCGATCGGATCTACAAGACCTATGCCGACCAGTGCCTGCAGC

TGGTGCAGCTGGATTGGGAGAACCTGAGCGCCGCCATCGACTCCTATAGA

AAGGAGAAAACCGAGGAGACAAGGAACGCCCTGATCGAGGAGCAGGCCAC

ATATCGCAATGCCATCCACGACTACTTCATCGGCCGGACAGACAACCTGA

CCGATGCCATCAATAAGAGACACGCCGAGATCTACAAGGGCCTGTTCAAG

GCCGAGCTGTTTAATGGCAAGGTGCTGAAGCAGCTGGGCACCGTGACCAC

AACCGAGCACGAGAACGCCCTGCTGCGGAGCTTCGACAAGTTTACAACCT

ACTTCTCCGGCTTTTATGAGAACAGGAAGAACGTGTTCAGCGCCGAGGAT

ATCAGCACAGCCATCCCACACCGCATCGTGCAGGACAACTTCCCCAAGTT

TAAGGAGAATTGTCACATCTTCACACGCCTGATCACCGCCGTGCCCAGCC

TGCGGGAGCACTTTGAGAACGTGAAGAAGGCCATCGGCATCTTCGTGAGC

ACCTCCATCGAGGAGGTGTTTTCCTTCCCTTTTTATAACCAGCTGCTGAC

ACAGACCCAGATCGACCTGTATAACCAGCTGCTGGGAGGAATCTCTCGGG

AGGCAGGCACCGAGAAGATCAAGGGCCTGAACGAGGTGCTGAATCTGGCC

ATCCAGAAGAATGATGAGACAGCCCACATCATCGCCTCCCTGCCACACAG

ATTCATCCCCCTGTTTAAGCAGATCCTGTCCGATAGGAACACCCTGTCTT

TCATCCTGGAGGAGTTTAAGAGCGACGAGGAAGTGATCCAGTCCTTCTGC

AAGTACAAGACACTGCTGAGAAACGAGAACGTGCTGGAGACAGCCGAGGC

CCTGTTTAACGAGCTGAACAGCATCGACCTGACACACATCTTCATCAGCC

ACAAGAAGCTGGAGACAATCAGCAGCGCCCTGTGCGACCACTGGGATACA

CTGAGGAATGCCCTGTATGAGCGGAGAATCTCCGAGCTGACAGGCAAGAT

CACCAAGTCTGCCAAGGAGAAGGTGCAGCGCAGCCTGAAGCACGAGGATA

TCAACCTGCAGGAGATCATCTCTGCCGCAGGCAAGGAGCTGAGCGAGGCC

TTCAAGCAGAAAACCAGCGAGATCCTGTCCCACGCACACGCCGCCCTGGA

TCAGCCACTGCCTACAACCCTGAAGAAGCAGGAGGAGAAGGAGATCCTGA

AGTCTCAGCTGGACAGCCTGCTGGGCCTGTACCACCTGCTGGACTGGTTT

GCCGTGGATGAGTCCAACGAGGTGGACCCCGAGTTCTCTGCCCGGCTGAC

CGGCATCAAGCTGGAGATGGAGCCTTCTCTGAGCTTCTACAACAAGGCCA

GAAATTATGCCACCAAGAAGCCCTACTCCGTGGAGAAGTTCAAGCTGAAC

TTTCAGATGCCTACACTGGCCTCTGGCTGGGACGTGAATAAGGAGAAGAA

CAATGGCGCCATCCTGTTTGTGAAGAACGGCCTGTACTATCTGGGCATCA

TGCCAAAGCAGAAGGGCAGGTATAAGGCCCTGAGCTTCGAGCCCACAGAG

AAAACCAGCGAGGGCTTTGATAAGATGTACTATGACTACTTCCCTGATGC

CGCCAAGATGATCCCAAAGTGCAGCACCCAGCTGAAGGCCGTGACAGCCC

ACTTTCAGACCCACACAACCCCCATCCTGCTGTCCAACAATTTCATCGAG

CCTCTGGAGATCACAAAGGAGATCTACGACCTGAACAATCCTGAGAAGGA

GCCAAAGAAGTTTCAGACAGCCTACGCCAAGAAAACCGGCGACCAGAAGG

GCTACAGAGAGGCCCTGTGCAAGTGGATCGACTTCACAAGGGATTTTCTG

TCCAAGTATACCAAGACAACCTCTATCGATCTGTCTAGCCTGCGGCCATC

CTCTCAGTATAAGGACCTGGGCGAGTACTATGCCGAGCTGAATCCCCTGC
```

-continued

TGTACCACATCAGCTTCCAGAGAATCGCCGAGAAGGAGATCATGGATGCC

GTGGAGACAGGCAAGCTGTACCTGTTCCAGATCTATAACAAGGACTTTGC

CAAGGGCCACCACGGCAAGCCTAATCTGCACACACTGTATTGGACCGGCC

TGTTTTCTCCAGAGAACCTGGCCAAGACAAGCATCAAGCTGAATGGCCAG

GCCGAGCTGTTCTACCGCCCTAAGTCCAGGATGAAGAGGATGGCACACCG

GCTGGGAGAGAAGATGCTGAACAAGAAGCTGAAGGATCAGAAAACCCCAA

TCCCCGACACCCTGTACCAGGAGCTGTACGACTATGTGAATCACAGACTG

TCCCACGACCTGTCTGATGAGGCCAGGGCCCTGCTGCCCAACGTGATCAC

CAAGGAGGTGTCTCACGAGATCATCAAGGATAGGCGCTTTACCAGCGACA

AGTTCTTTTTCCACGTGCCTATCACACTGAACTATCAGGCCGCCAATTCC

CCATCTAAGTTCAACCAGAGGGTGAATGCCTACCTGAAGGAGCACCCCGA

GACACCTATCATCGGCATCGATCGGGGCGAGAGAAACCTGATCTATATCA

CAGTGATCGACTCCACCGGCAAGATCCTGGAGCAGCGGAGCCTGAACACC

ATCCAGCAGTTTGATTACCAGAAGAAGCTGGACAACAGGGAGAAGGAGAG

GGTGGCAGCAAGGCAGGCCTGGTCTGTGGTGGGCACAATCAAGGATCTGA

AGCAGGGCTATCTGAGCCAGGTCATCCACGAGATCGTGGACCTGATGATC

CACTACCAGGCCGTGGTGGTGCTGGAGAACCTGAATTTCGGCTTTAAGAG

CAAGAGGACCGGCATCGCCGAGAAGGCCGTGTACCAGCAGTTCGAGAAGA

TGCTGATCGATAAGCTGAATTGCCTGGTGCTGAAGGACTATCCAGCAGAG

AAAGTGGGAGGCGTGCTGAACCCATACCAGCTGACAGACCAGTTCACCTC

CTTTGCCAAGATGGGCACCCAGTCTGGCTTCCTGTTTTACGTGCCTGCCC

CATATACATCTAAGATCGATCCCCTGACCGGCTTCGTGGACCCCTTCGTG

TGGAAAACCATCAAGAATCACGAGAGCCGCAAGCACTTCCTGGAGGGCTT

CGACTTTCTGCACTACGACGTGAAAACCGGCGACTTCATCCTGCACTTTA

AGATGAACAGAAATCTGTCCTTCCAGAGGGGCCTGCCCGGCTTTATGCCT

GCATGGGATATCGTGTTCGAGAAGAACGAGACACAGTTTGACGCCAAGGG

CACCCCTTTCATCGCCGGCAAGAGAATCGTGCCAGTGATCGAGAATCACA

GATTCACCGGCAGATACCGGGACCTGTATCCTGCCAACGAGCTGATCGCC

CTGCTGGAGGAGAAGGGCATCGTGTTCAGGGATGGCTCCAACATCCTGCC

AAAGCTGCTGGAGAATGACGATTCTCACGCCATCGACACCATGGTGGCCC

TGATCCGCAGCGTGCTGCAGATGCGGAACTCCAATGCCGCCACAGGCGAG

GACTATATCAACAGCCCCGTGCGCGATCTGAATGGCGTGTGCTTCGACTC

CCGGTTTCAGAACCCAGAGTGGCCCATGGACGCCGATGCCAATGGCGCCT

ACCACATCGCCCTGAAGGGCCAGCTGCTGCTGAATCACCTGAAGGAGAGC

AAGGATCTGAAGCTGCAGAACGGCATCTCCAATCAGGACTGGCTGGCCTA

CATCCAGGAGCTGCGCAACAAGCGTCCTGCTGCTACTAAGAAAGCTGGTC

AAGCTAAGAAAAAGAAATAA.

In one embodiment, the Cpf1 protein is encoded by SEQ ID NO:2. This sequence can be codon optimized, can differ due to the degeneracy of the genetic code, can be similar, or share substantial identity, to SEQ ID NO:2, but still retain nuclease activity.

LbCpf1 sequence (SEQ ID NO: 2)

(SEQ ID NO: 2)

ATGGCCCCAAAGAAGAAGCGGAAGGTCGGTATCCACGGAGTCCCAGCAGC

CAGCAAGCTGGAGAAGTTTACAAACTGCTACTCCCTGTCTAAGACCCTGA

GGTTCAAGGCCATCCCTGTGGGCAAGACCCAGGAGAACATCGACAATAAG

CGGCTGCTGGTGGAGGACGAGAAGAGAGCCGAGGATTATAAGGGCGTGAA

GAAGCTGCTGGATCGCTACTATCTGTCTTTTATCAACGACGTGCTGCACA

GCATCAAGCTGAAGAATCTGAACAATTACATCAGCCTGTTCCGGAAGAAA

ACCAGAACCGAGAAGGAGAATAAGGAGCTGGAGAACCTGGAGATCAATCT

GCGGAAGGAGATCGCCAAGGCCTTCAAGGGCAACGAGGGCTACAAGTCCC

TGTTTAAGAAGGATATCATCGAGACAATCCTGCCAGAGTTCCTGGACGAT

AAGGACGAGATCGCCCTGGTGAACAGCTTCAATGGCTTTACCACAGCCTT

CACCGGCTTCTTTGATAACAGAGAGAATATGTTTTCCGAGGAGGCCAAGA

GCACATCCATCGCCTTCAGGTGTATCAACGAGAATCTGACCCGCTACATC

TCTAATATGGACATCTTCGAGAAGGTGGACGCCATCTTTGATAAGCACGA

GGTGCAGGAGATCAAGGAGAAGATCCTGAACAGCGACTATGATGTGGAGG

ATTTCTTTGAGGGCGAGTTCTTTAACTTTGTGCTGACACAGGAGGGCATC

GACGTGTATAACGCCATCATCGGCGGCTTCGTGACCGAGAGCGGCGAGAA

GATCAAGGGCCTGAACGAGTACATCAACCTGTATAATCAGAAAACCAAGC

AGAAGCTGCCTAAGTTTAAGCCACTGTATAAGCAGGTGCTGAGCGATCGG

GAGTCTCTGAGCTTCTACGGCGAGGGCTATACATCCGATGAGGAGGTGCT

GGAGGTGTTTAGAAACACCCTGAACAAGAACAGCGAGATCTTCAGCTCCA

TCAAGAAGCTGGAGAAGCTGTTCAAGAATTTTGACGAGTACTCTAGCGCC

GGCATCTTTGTGAAGAACGGCCCCGCCATCAGCACAATCTCCAAGGATAT

CTTCGGCGAGTGGAACGTGATCCGGGACAAGTGGAATGCCGAGTATGACG

ATATCCACCTGAAGAAGAAGGCCGTGGTGACCGAGAAGTACGAGGACGAT

CGGAGAAAGTCCTTCAAGAAGATCGGCTCCTTTTCTCTGGAGCAGCTGCA

GGAGTACGCCGACGCCGATCTGTCTGTGGTGGAGAAGCTGAAGGAGATCA

TCATCCAGAAGGTGGATGAGATCTACAAGGTGTATGGCTCCTCTGAGAAG

CTGTTCGACGCCGATTTTGTGCTGGAGAAGAGCCTGAAGAAGAACGACGC

CGTGGTGGCCATCATGAAGGACCTGCTGGATTCTGTGAAGAGCTTCGAGA

ATTACATCAAGGCCTTCTTTGGCGAGGGCAAGGAGACAAACAGGGACGAG

TCCTTCTATGGCGATTTTGTGCTGGCCTACGACATCCTGCTGAAGGTGGA

CCACATCTACGATGCCATCCGCAATTATGTGACCCAGAAGCCCTACTCTA

AGGATAAGTTCAAGCTGTATTTTCAGAACCCTCAGTTCATGGGCGGCTGG

GACAAGGATAAGGAGACAGACTATCGGGCCACCATCCTGAGATACGGCTC

CAAGTACTATCTGGCCATCATGGATAAGAAGTACGCCAAGTGCCTGCAGA

AGATCGACAAGGACGATGTGAACGGCAATTACGAGAAGATCAACTATAAG

CTGCTGCCCGGCCCTAATAAGATGCTGCCAAAGGTGTTCTTTTCTAAGAA

GTGGATGGCCTACTATAACCCCAGCGAGGACATCCAGAAGATCTACAAGA

ATGGCACATTCAAGAAGGGCGATATGTTTAACCTGAATGACTGTCACAAG

CTGATCGACTTCTTTAAGGATAGCATCTCCCGGTATCCAAAGTGGTCCAA

-continued

```
TGCCTACGATTTCAACTTTTCTGAGACAGAGAAGTATAAGGACATCGCCG

GCTTTTACAGAGAGGTGGAGGAGCAGGGCTATAAGGTGAGCTTCGAGTCT

GCCAGCAAGAAGGAGGTGGATAAGCTGGTGGAGGAGGGCAAGCTGTATAT

GTTCCAGATCTATAACAAGGACTTTTCCGATAAGTCTCACGGCACACCCA

ATCTGCACACCATGTACTTCAAGCTGCTGTTTGACGAGAACAATCACGGA

CAGATCAGGCTGAGCGGAGGAGCAGAGCTGTTCATGAGGCGCGCCTCCCT

GAAGAAGGAGGAGCTGGTGGTGCACCCAGCCAACTCCCCTATCGCCAACA

AGAATCCAGATAATCCCAAGAAAACCACAACCCTGTCCTACGACGTGTAT

AAGGATAAGAGGTTTTCTGAGGACCAGTACGAGCTGCACATCCCAATCGC

CATCAATAAGTGCCCCAAGAACATCTTCAAGATCAATACAGAGGTGCGCG

TGCTGCTGAAGCACGACGATAACCCCTATGTGATCGGCATCGATAGGGGC

GAGCGCAATCTGCTGTATATCGTGGTGGTGGACGGCAAGGGCAACATCGT

GGAGCAGTATTCCCTGAACGAGATCATCAACAACTTCAACGGCATCAGGA

TCAAGACAGATTACCACTCTCTGCTGGACAAGAAGGAGAAGGAGAGGTTC

GAGGCCCGCCAGAACTGGACCTCCATCGAGAATATCAAGGAGCTGAAGGC

CGGCTATATCTCTCAGGTGGTGCACAAGATCTGCGAGCTGGTGGAGAAGT

ACGATGCCGTGATCGCCCTGGAGGACCTGAACTCTGGCTTTAAGAATAGC

CGCGTGAAGGTGGAGAAGCAGGTGTATCAGAAGTTCGAGAAGATGCTGAT

CGATAAGCTGAACTACATGGTGGACAAGAAGTCTAATCCTTGTGCAACAG

GCGGCGCCCTGAAGGGCTATCAGATCACCAATAAGTTCGAGAGCTTTAAG

TCCATGTCTACCCAGAACGGCTTCATCTTTTACATCCCTGCCTGGCTGAC

ATCCAAGATCGATCCATCTACCGGCTTTGTGAACCTGCTGAAAACCAAGT

ATACCAGCATCGCCGATTCCAAGAAGTTCATCAGCTCCTTTGACAGGATC

ATGTACGTGCCCGAGGAGGATCTGTTCGAGTTTGCCCTGGACTATAAGAA

CTTCTCTCGCACAGACGCCGATTACATCAAGAAGTGGAAGCTGTACTCCT

ACGGCAACCGGATCAGAATCTTCCGGAATCCTAAGAAGAACAACGTGTTC

GACTGGGAGGAGGTGTGCCTGACCAGCGCCTATAAGGAGCTGTTCAACAA

GTACGGCATCAATTATCAGCAGGGCGATATCAGAGCCCTGCTGTGCGAGC

AGTCCGACAAGGCCTTCTACTCTAGCTTTATGGCCCTGATGAGCCTGATG

CTGCAGATGCGGAACAGCATCACAGGCCGCACCGACGTGGATTTTCTGAT

CAGCCCTGTGAAGAACTCCGACGGCATCTTCTACGATAGCCGGAACTATG

AGGCCCAGGAGAATGCCATCCTGCCAAAGAACGCCGACGCCAATGGCGCC

TATAACATCGCCAGAAAGGTGCTGTGGGCCATCGGCCAGTTCAAGAAGGC

CGAGGACGAGAAGCTGGATAAGGTGAAGATCGCCATCTCTAACAAGGAGT

GGCTGGAGTACGCCCAGACCAGCGTGAAGCACAAGCGTCCTGCTGCTACT

AAGAAAGCTGGTCAAGCTAAGAAAAAGAAATAA.
```

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Tunable Oligonucleotide Switches to Modulate CRISPR-Cpf1 Mediated Genome Editing The CRISPR-Cpf1 system employs a single stranded CRISPR RNA (crRNA) to guide genome editing of target DNA sequences. To modulate genome editing activity of Cpf1, a series of crRNA variants were designed containing crRNA chimeras and duplexes. Single-stranded crRNA chimeras composed of mixed DNA and RNA nucleotides completely lost gene-cutting activity and crRNA is not well-tolerated for deoxynucleotide substitutions. Furthermore, crRNA duplexes formed by introduction of oligonucleotides (10-43 nucleotides) complementary to various regions of crRNA were capable of regulating activity of the Cpf1 endonuclease. For example, phosphorothioate (PS)-modified DNA/crRNA hybrid blocked the function of the Cpf1. More importantly, this PS-modified DNA was able to regulate Cpf1 activity in a time- and dose-dependent manner. Consequently, oligonucleotides provide tunable switches to modulate Cpf1 mediated genome editing.

Cpf1 (CRISPR from *Prevotella* and *Francisella* 1) is one of the CRISPR associated effector endonucleases, which induces double stranded DNA breaks under the guidance of a single CRISPR RNA (crRNA)[1]. The wild-type crRNA of CRISPR-Cpf1 system comprises a 5'-handle engaging Cpf1 recognition and a guide segment interacting with targeted DNA sequences through complimentary bindings[1-3]. Crystal structure of the Cpf1-crRNA-dsDNA complex uncovers the unique T-rich PAM recognition and cleavage mechanism by Cpf1[2,4-7]. Based on its unique gene editing properties, the CRISPR-Cpf1 system has recently been applied in diverse eukaryotic species including plants and animals to achieve targeted genome editing[8-18].

Figure 1B:
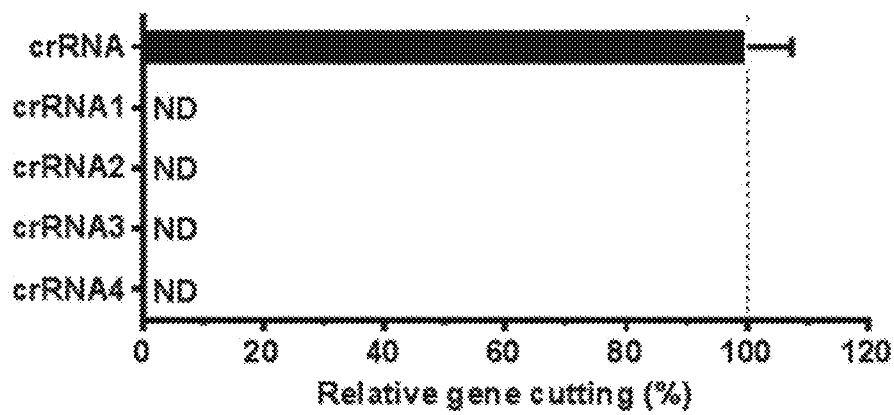

Although the CRISPR system offers a powerful platform for genome editing, a number of challenges exist for its therapeutic applications including gene editing efficiency and potential side effects[19]. Previously, extensive efforts have been made to improve gene editing efficiency[2,20-22] Meanwhile, researchers investigated diverse approaches to modulate the activity of the CRISPR system. Especially, when severe side effects occur for the system, it is essential to prepare an effective and fast mechanism to switch off its function. Recently, anti-CRISPR proteins from bacteriophage or bacteria were discovered to inhibit the function of *Listeria monocytogenes* or *Neisseria meningitidis* CRISPR-Cas923.24. In addition, multiple strategies such as chemical-, temperature- and light-triggered approaches were developed to regulate the CRISPR-Cas9 system[25,26]. However, no method is currently available to effectively regulate the CRISPR-Cpf1 system including upregulation, downregulation, and complete inactivation. In this example, an array of oligonucleotides is reported as adjustable switches to fine-tune the Cpf1 activity. First, in order to understand the applicability of Cpf1 crRNA, three crRNA chimeras crRNA1-crRNA3 were designed (FIG. 1*a*), by substituting crRNA nucleotides (full crRNA, 5'-handle or guide segment) with their corresponding DNA bases. Their activity to mediate DNMT1 gene cleavage in HEK293T cells was tested in the presence of AsCpf1 plasmid. The wild-type crRNA targeting DNMT1 site 3 served as a control group. None of the three substitution patterns resulted in detectable gene cutting (FIG. 1*b*). Meanwhile, in the crystal structure of crRNA-AsCpf1-DNA complex, twenty-one nucleotides were identified which displayed trivial interactions with the Cpf1 and target DNA sequences. These nucleotides were replaced with DNA bases and synthesized crRNA4 chimera (FIG. 1*a*), which also showed undetectable activity (FIG. 1*b*). These results indicate that a relatively large portion of deoxynucleotides substitution on the crRNA is not favorable for Cpf1 mediated gene cutting.

Figure 3A:
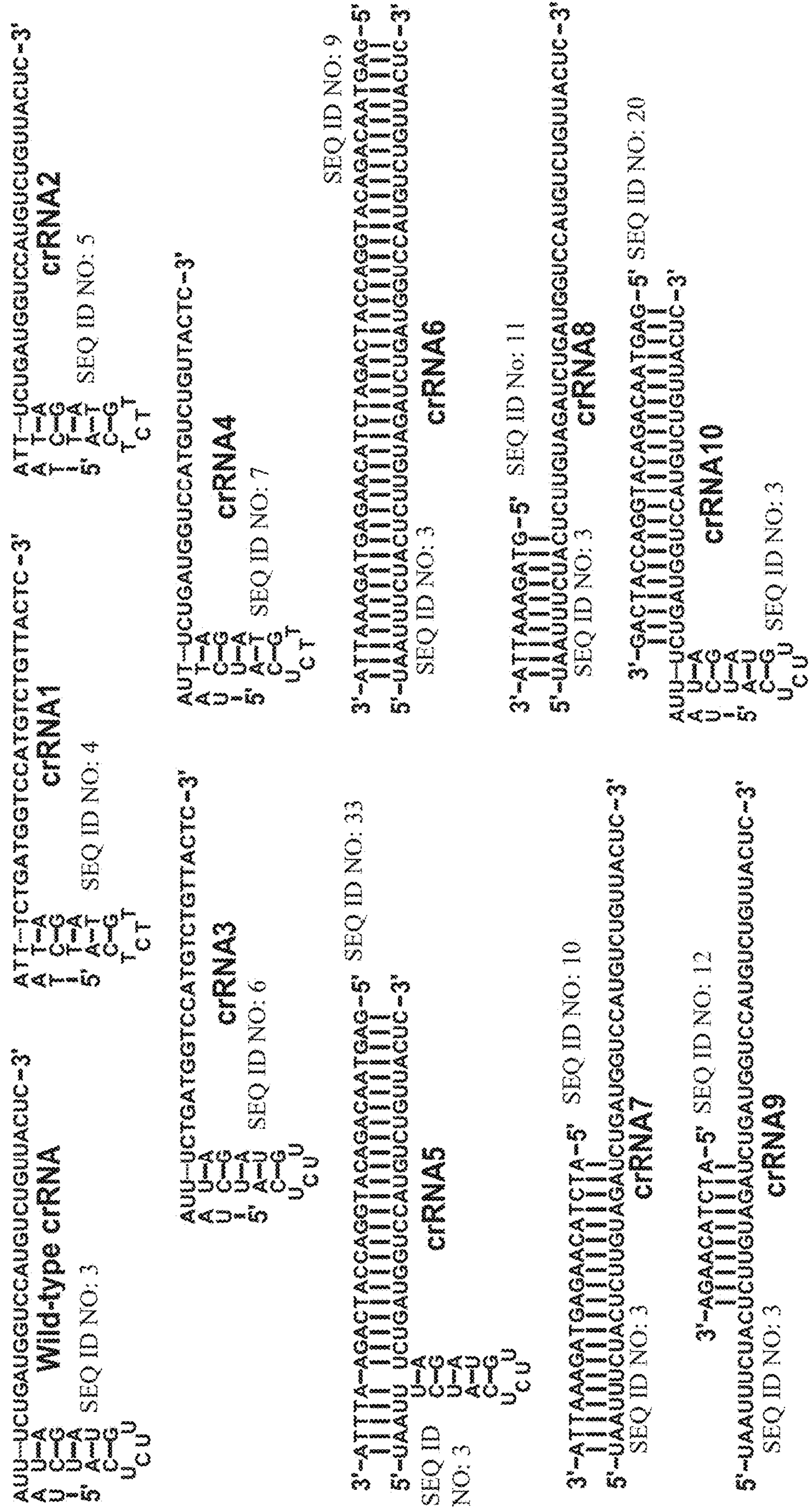
FIG. 3. Overall structure of wild-type crRNA and its variants. The light grey letters denote the unmodified RNA base (see crRNA19 and 20). The black letters denote unmodified DNA base (see crRNA1 to crRNA14). The dark grey letters denote PS-linkage modified DNA (crRNA15, 16, 17). The intermediate grey letters denote 2'-fluoro modified RNA (crRNA21 and 22). The light black letters denote 2'-O-methyl modified RNA (crRNA23, 24, and 25). The dash represents the hydrogen-bond interaction between paired bases.
Figure 3B:
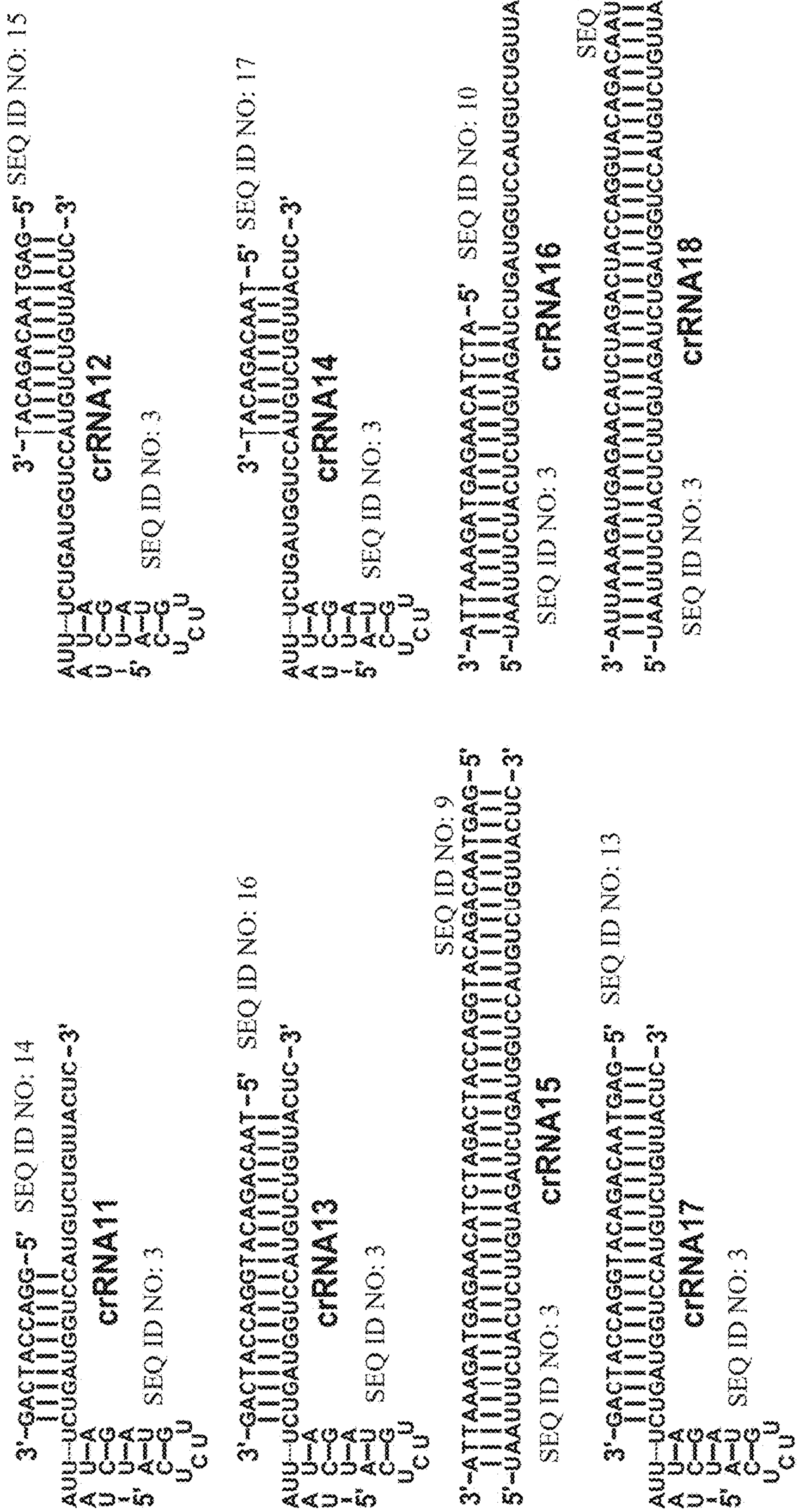
Figure 3C:
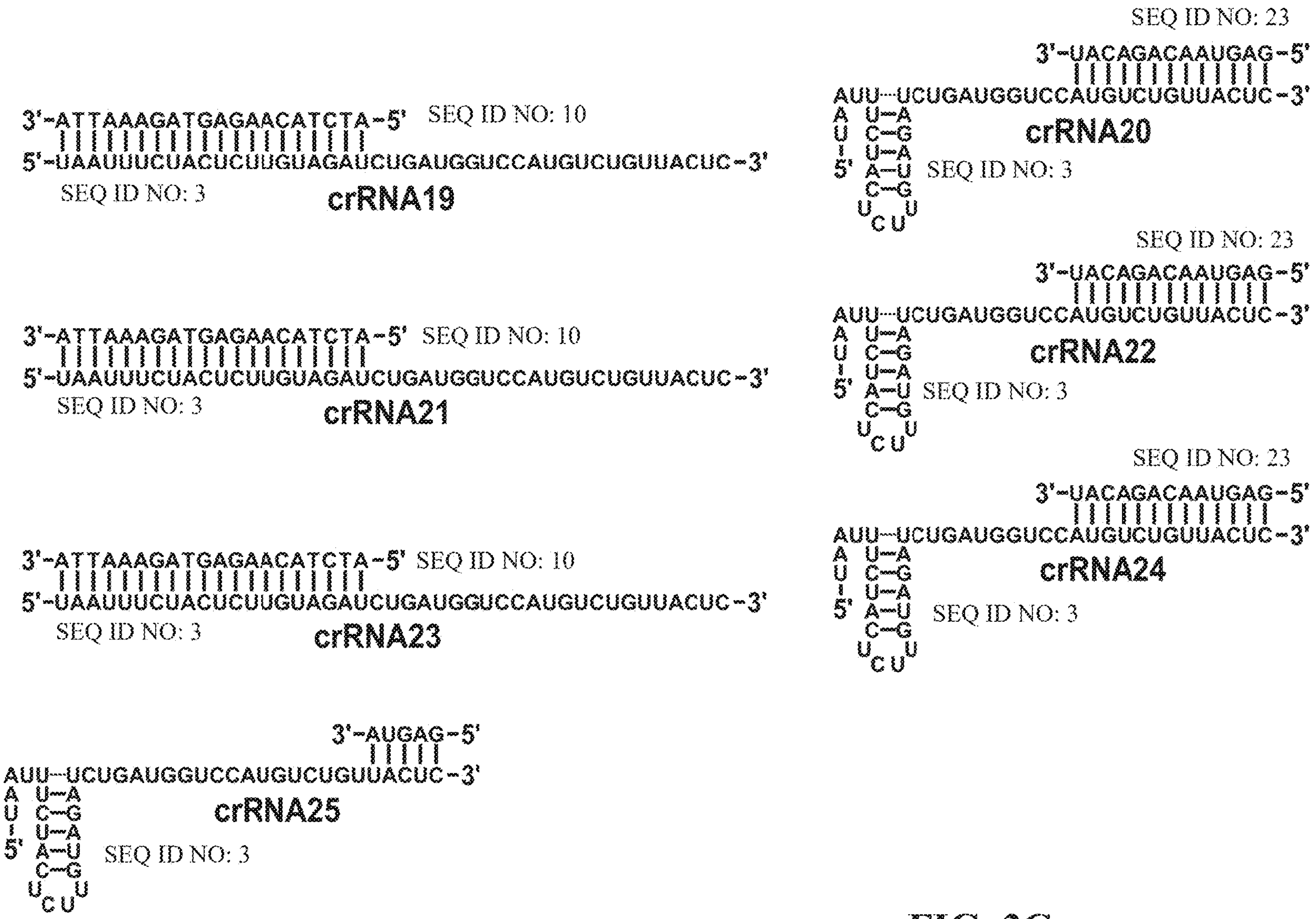
Figure 4A:
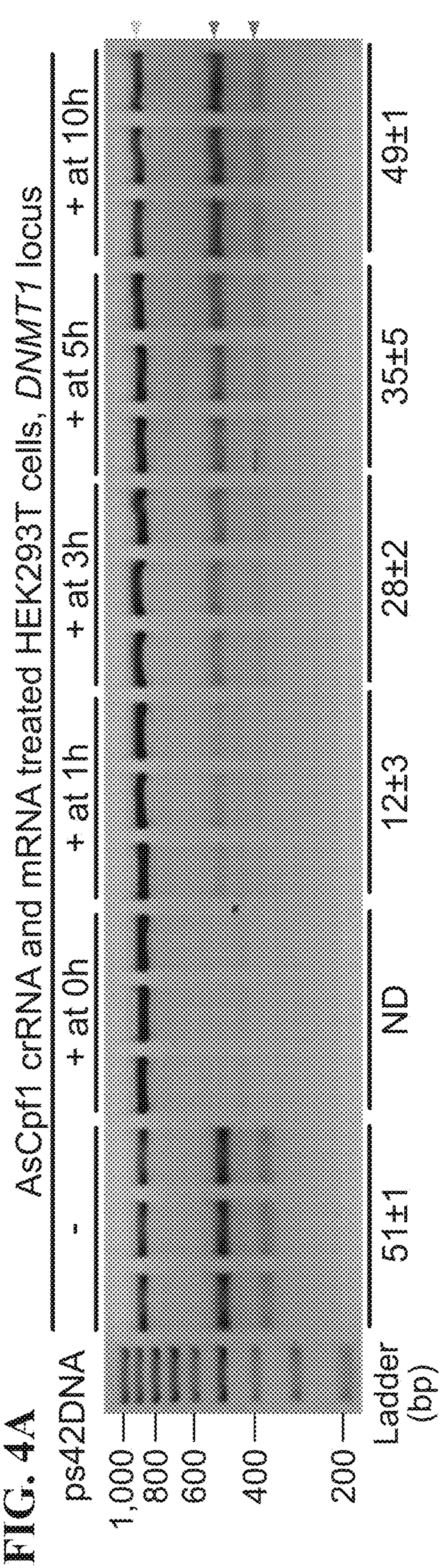
FIGS. 4A-4F. Inhibition effects of phosphorothioated DNA oligonucleotides on Cpf1-mediated gene editing in human cells.
Figure 4B:
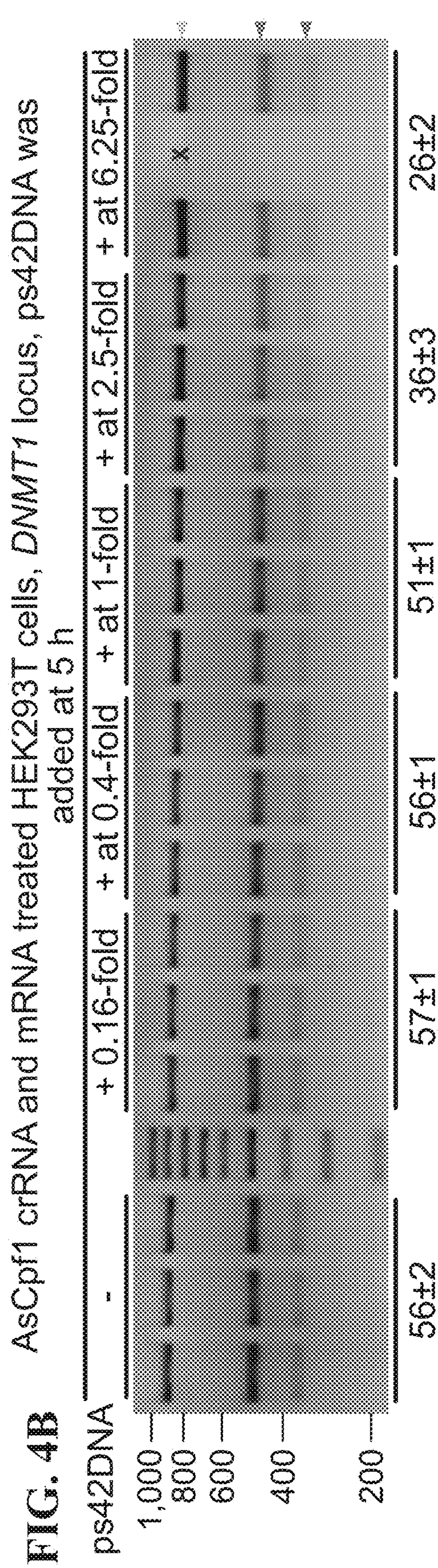
Figure 4C:
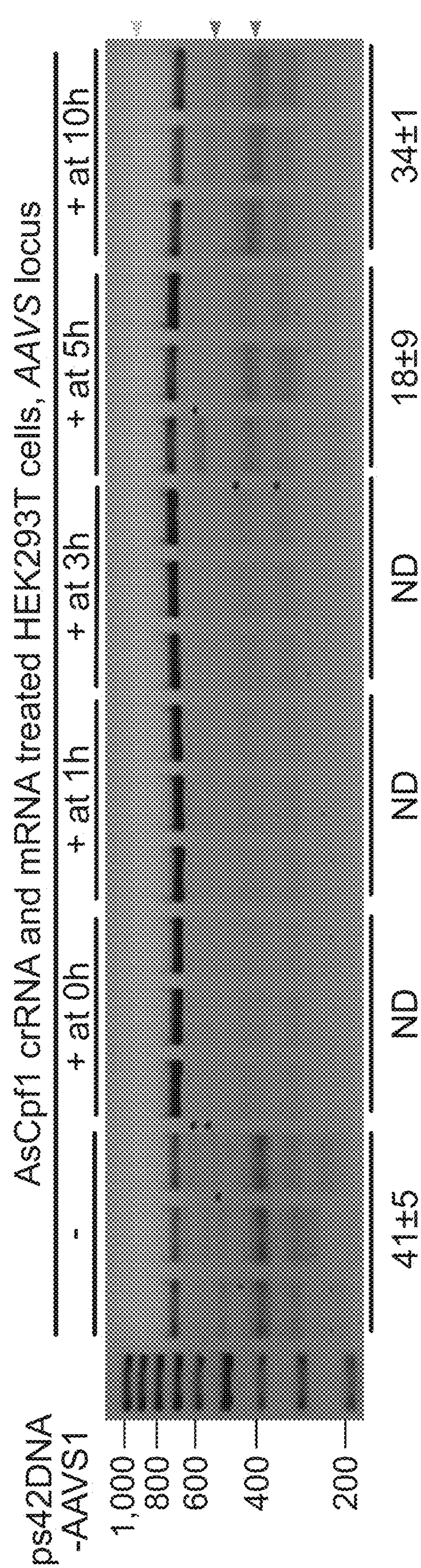
Figure 4D:
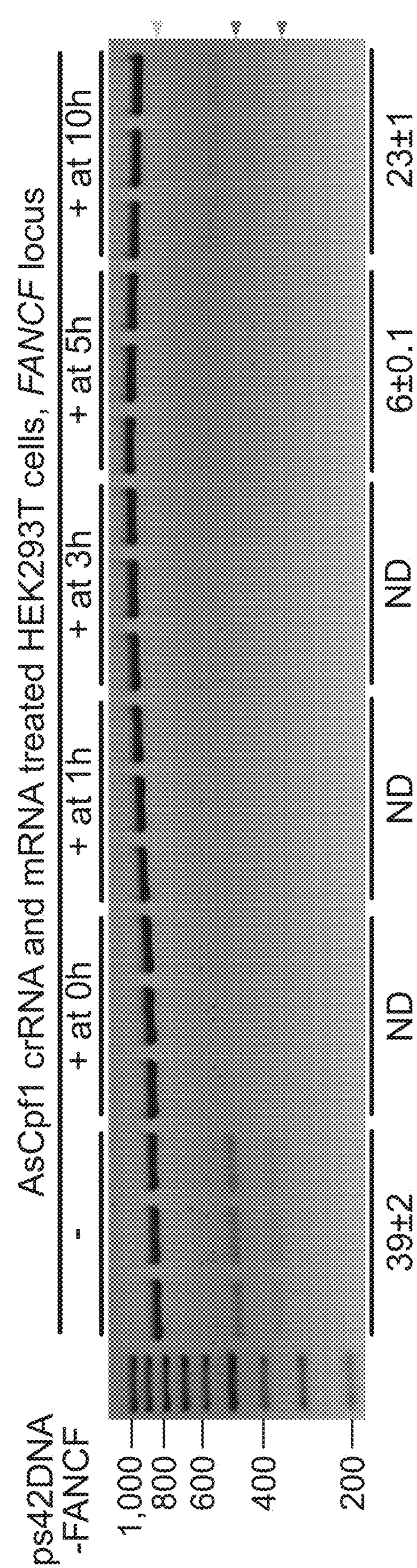
Figure 4E:
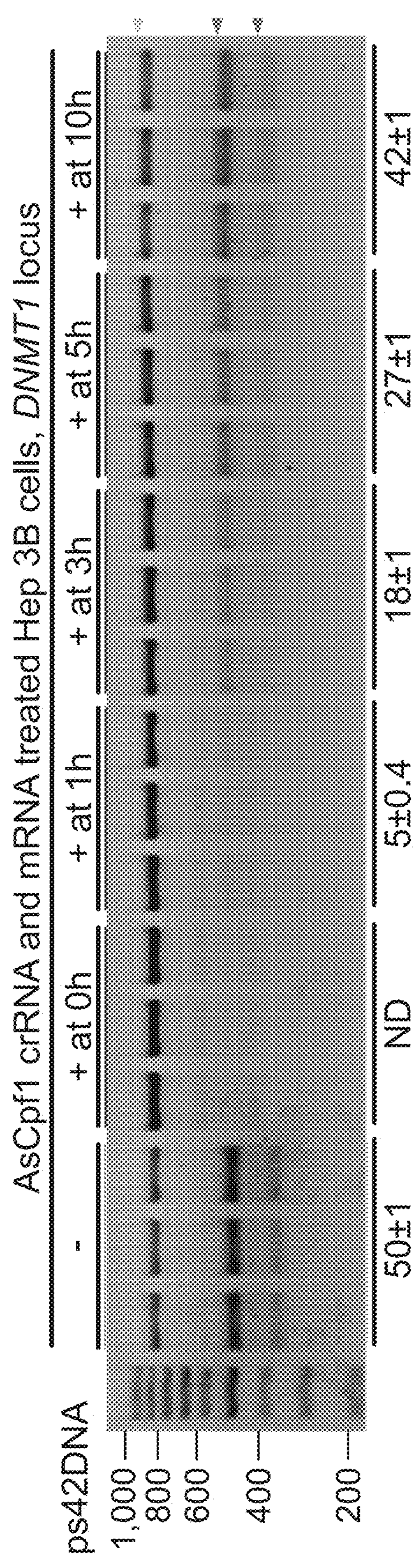
Figure 4F:
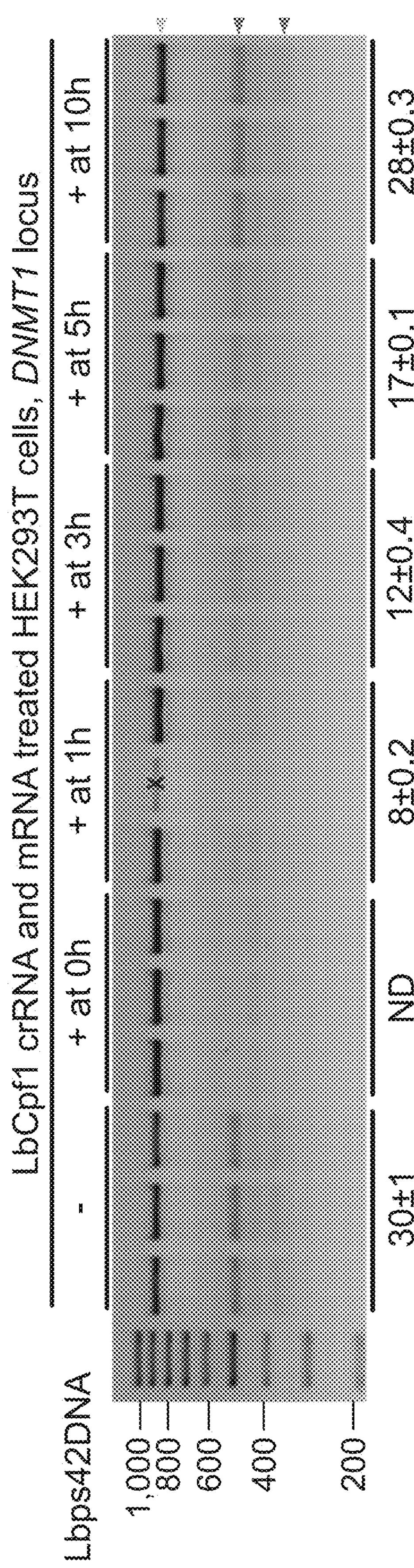

Next, in attempts to effectively regulate Cpf1-mediated genome editing, oligonucleotides were likely important regulators for gene cutting activity of the Cpf1. Oligonucleotides are short single stranded DNA or RNA molecules which have been widely used for diverse application[27]. Given the crucial role of crRNA in the Cpf1-crRNA-DNA complex, a series of oligonucleotides complimentary to crRNA were designed and synthesized (10-43 nucleotides, Table 1). Their corresponding crRNA duplexes are shown in FIG. 3.

Figure 1C:
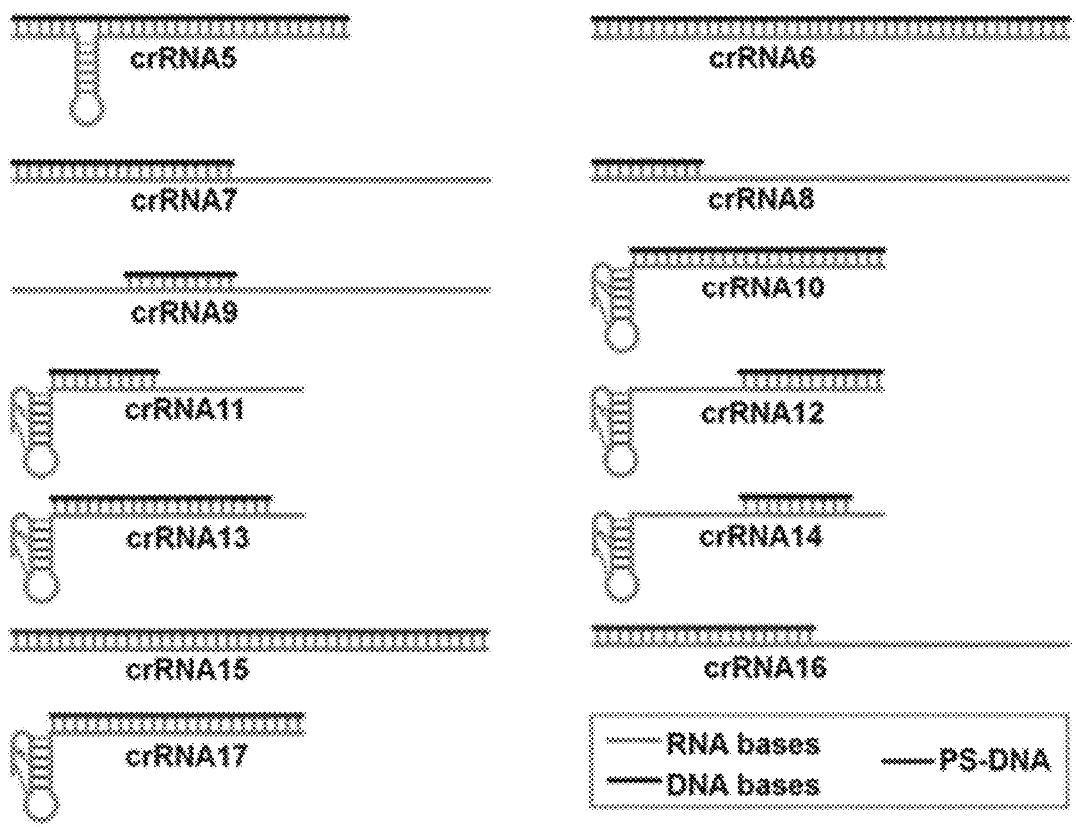
Figure 1D:
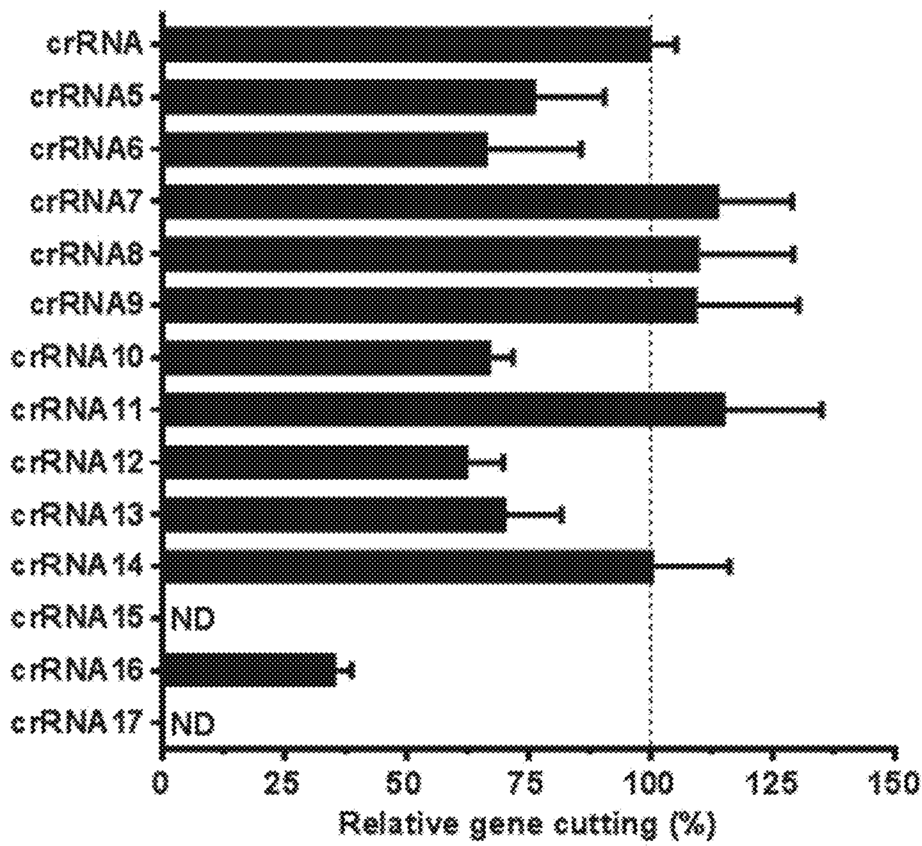
Figure 1E:
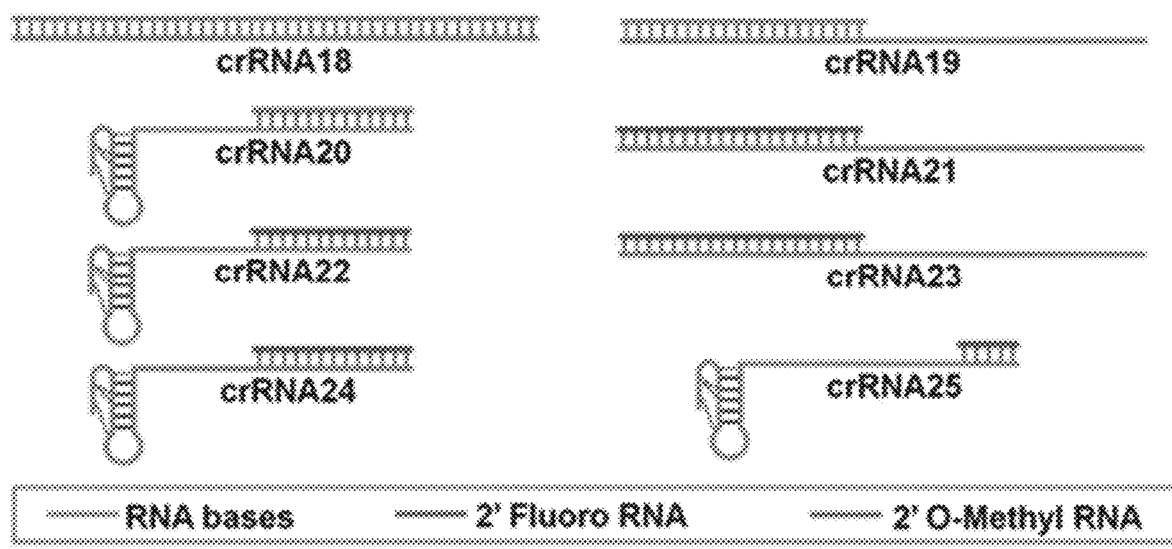
Figure 1F:
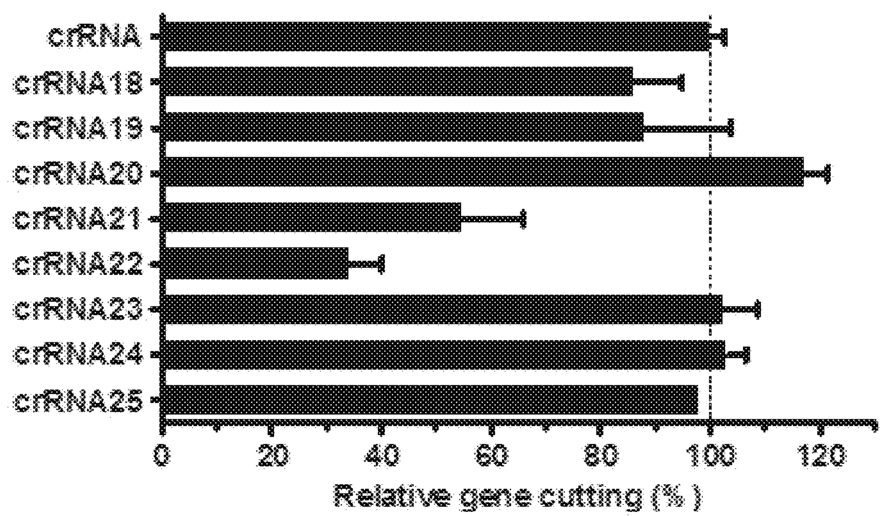

The first set is DNA-crRNA duplexes formed by hybridization of unmodified or phosphorothioate (PS)-modified DNA oligonucleotides with crRNA at different regions (crRNA5 to crRNA17, FIG. 1*c*). As shown in FIG. 1*d*, several crRNA duplexes including crRNA7, crRNA8, crRNA9, crRNA11 and crRNA14 showed comparable or slightly higher activity compared to the crRNA, while the rest duplexes crRNA5, crRNA6, crRNA10, crRNA12, crRNA13, crRNA15, crRNA16 and crRNA17 down-regulated the gene cutting. Interestingly, all three duplexes bearing PS linkages in DNA oligonucleotides dramatically reduced the gene cutting efficiency (FIG. 1*d*). Moreover, crRNA15 and crRNA17 completely blocked the function of Cpf1 (FIG. 1*d*). These results implied that oligonucleotides complimentary to the guide segment of crRNA may greatly affect the Cpf1 activity (crRNA15 and crRNA17 vs crRNA16). On the basis of DNA-crRNA duplexes, a second type of RNA-crRNA duplexes were examined (FIG. 1*e*). In this case, unmodified, 2'-O-methyl and 2'-fluoro RNA oligonucleotides were used to produce unmodified RNA-crRNA (crRNA18-crRNA20), 2'-fluoro RNA-crRNA (crRNA21 and crRNA22), and 2'-OMe RNA-crRNA (crRNA23 and crRNA24) duplexes. The activity of crRNA18-crRNA20 was comparable to that of crRNA (FIG. 1*f*), showing that unmodified RNA oligonucleotides had little effects on gene cutting activity. crRNA21 and crRNA22 dramatically reduced the activity (FIG. 1*f*), therefore 2'-fluoro RNA oligonucleotides may not be preferred modifications to enhance gene cutting.

Figure 1G:
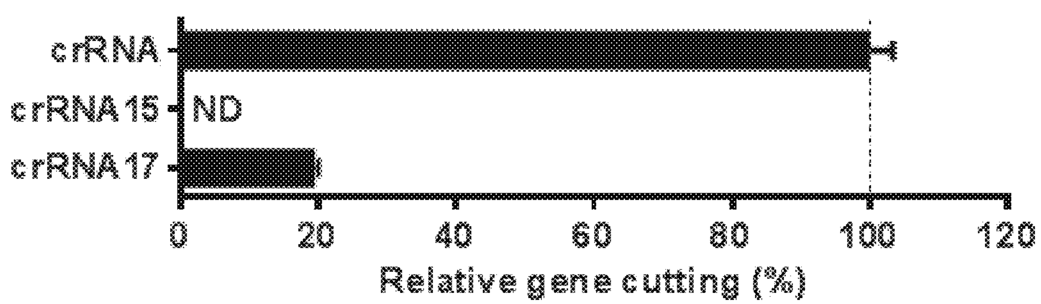

Recent studies reported that co-delivery of chemically modified Cpf1 mRNA and crRNA improved genome editing efficiency of Cpf1[21]. In order to further examine the effects of crRNA15 and crRNA17, HEK293T cells were treated with these crRNAs in the presence of Y'-modified Cpf1 mRNA. crRNA17 induced much lower gene cutting compared to crRNA, while crRNA15 fully switched off the Cpf1 activity under the same condition (FIG. 1*g*). These results show that PS-DNA covering both the handle and the guide segment of crRNA may be essential to fully inhibit the Cpf1 function. Hence, duplex crRNA15 containing 42-PS modified DNA oligonucleotide (termed as ps42DNA) was selected for further studies.

Figure 2A:
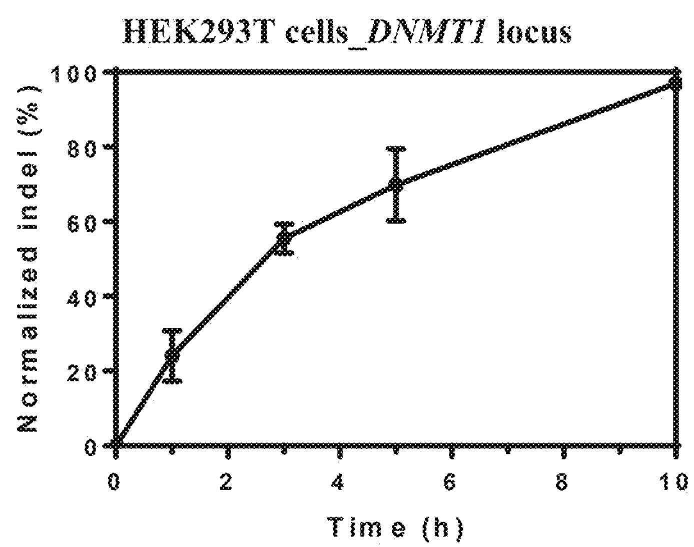
FIGS. 2A-2F. Inhibition effects of phosphorothioated DNA oligonucleotides on Cpf1-mediated gene editing in human cells.
Figure 2B:
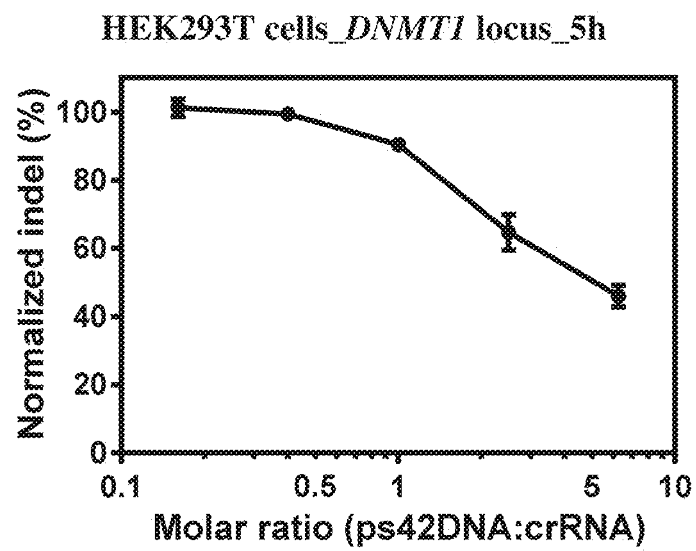

Considering the switch-off function of crRNA15, ps42DNA could serve as an effective inhibitor for the Cpf1 system. To further investigate this concept, three components (crRNA targeting DNMT1 locus, AsCpf1 mRNA, and ps42DNA) were separately formulated using Lipofectamine 3000 reagent, and then treated HEK293T cells. Amazingly, the process of genome editing was effectively interrupted when ps42DNA was added together with the other two components (time=0 h, FIG. 2*a*). Subsequently, cells were treated with crRNA plus AsCpf1 mRNA followed by the addition of Lipofectamine 3000 complexed ps42DNA at different time points in order to evaluate inhibition properties of ps42DNA. As shown in FIG. 2*a*, ps42DNA-treated groups gradually lost its inhibition activity on gene cutting. At the 10 h time point, ps42DNA was not able to affect the Cpf1 function. Next, the dose-dependency effects of ps42DNA were investigated at the 5 h time point. ps42DNA was found to act in a dose-dependent manner to regulate gene cutting (FIG. 2*b*). These observations indicated that time to add ps42DNA and dose of ps42DNA are two crucial factors to exert its switch-off function.

Figure 2C:
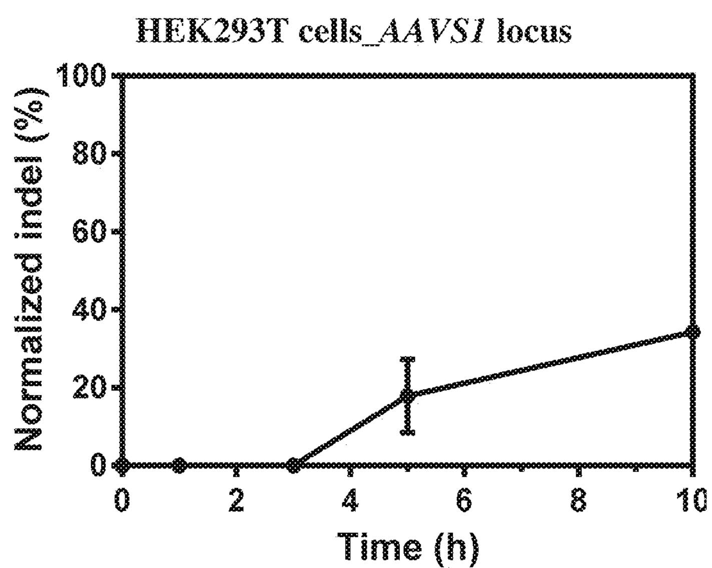
Figure 2D:
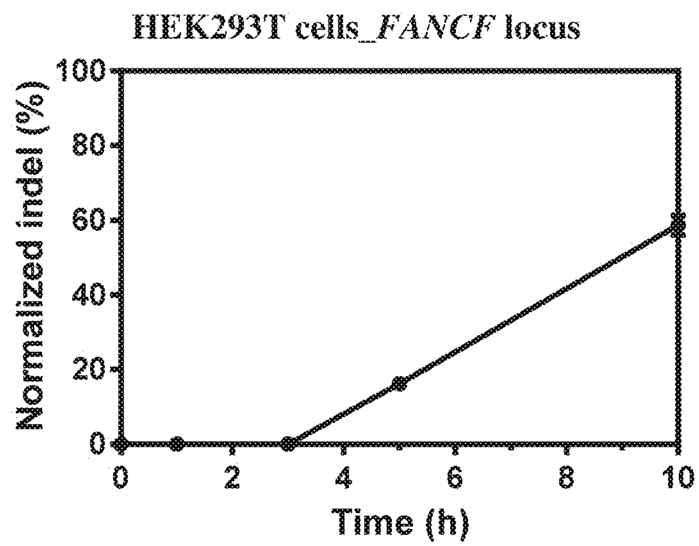
Figure 2E:
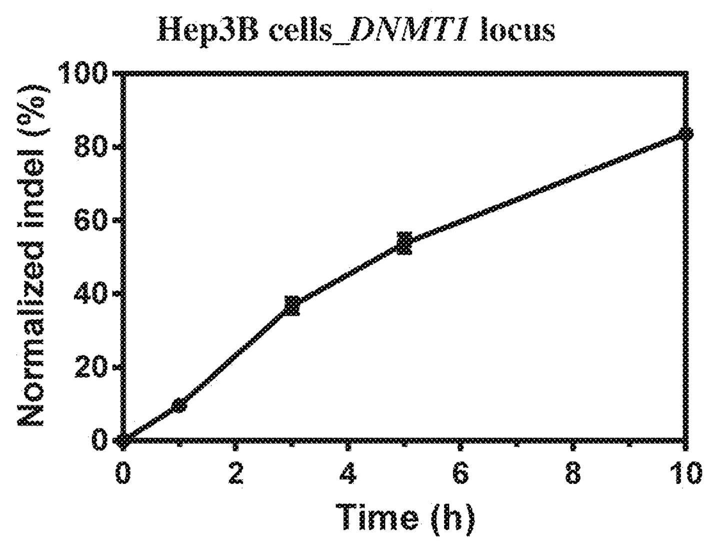
Figure 2F:
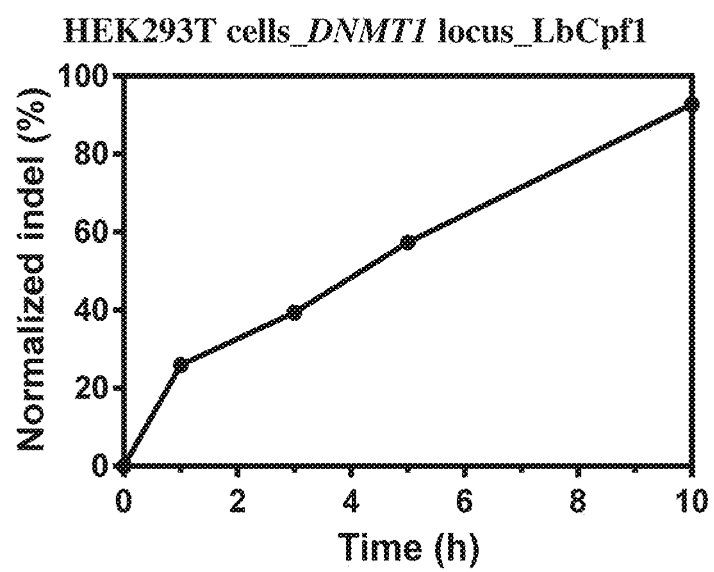

To investigate the applicability of ps42DNA, two additional phosphorothioated oligonucleotides complementary to crRNAs targeting the AAVS1 and FANCF genes were synthesized (termed ps42DNA-AAVS1 and ps42DNA-FANCF, respectively; Table 1)[28,29]. Consistent with the results mentioned above, both ps42DNA-AA and ps42DNA-FA showed time-dependent inhibition of gene cutting for their corresponding sequences. Their inhibition potency were higher than that of ps42DNA targeting DNMT1, as evidenced by undetectable cleavage at the time points 1, 3 and 5 h (FIG. 2*c,d*). In addition to HEK293T cell line, the effects of ps42DNA in Hep3B cells was evaluated. Similarly, ps42DNA showed dramatic inhibition of gene cutting in Hep3B cells (FIG. 2*c*). Next, the same strategy for LbCpf1 was examined (another one of the Cpf1 orthologues) using Lbps42DNA, which exhibited strong inhibition of gene cutting in a time dependent manner similar to ps42DNA (FIG. 2*f*). Collectively, ps42 modified DNA oligonucleotides are broadly applicable to inhibit Cpf1 activity at different gene loci in human cell lines.

Figure 5A:
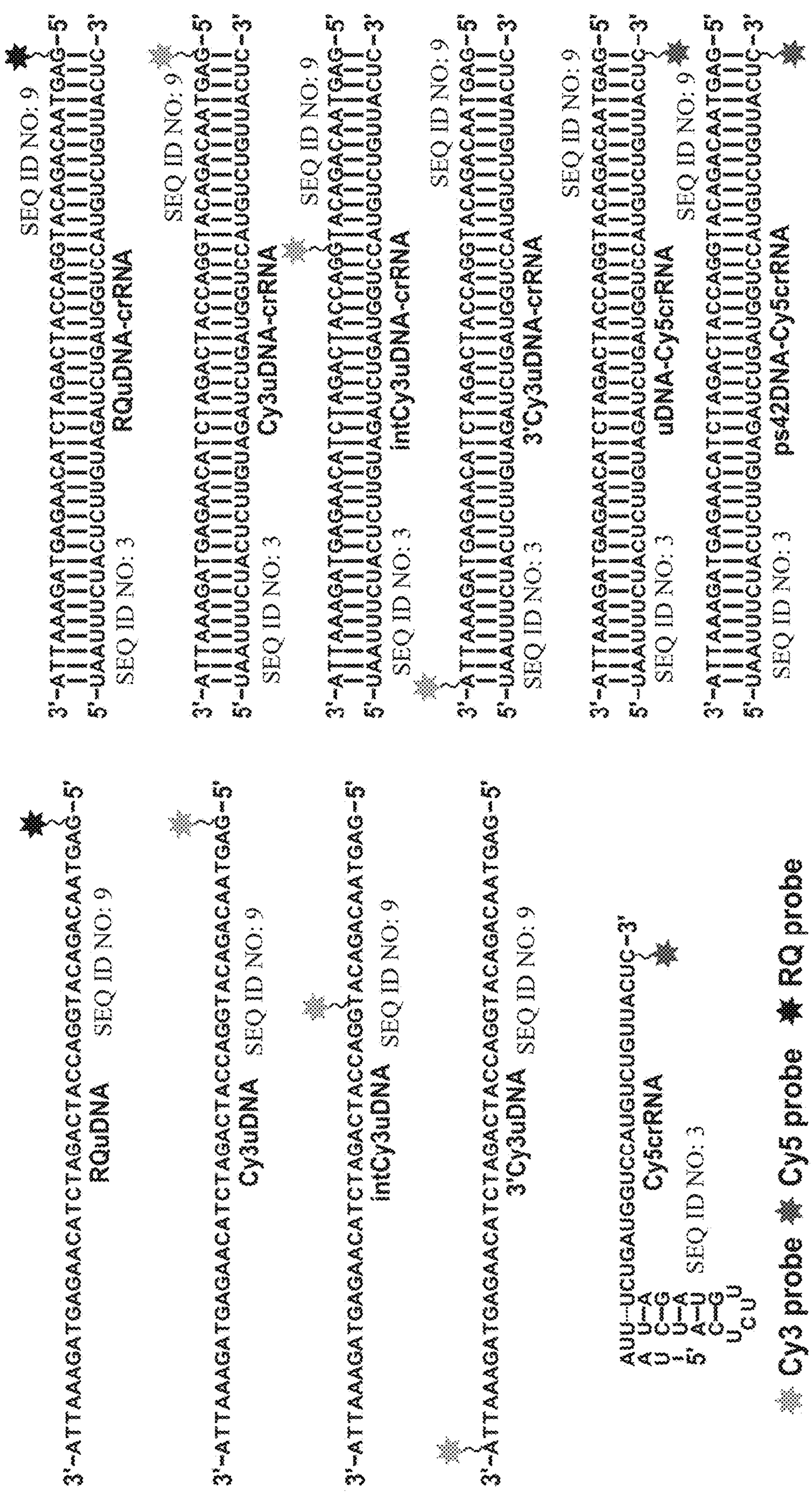
FIGS. 5A-5E. Gene cutting efficiency of fluorescently labeled crRNA and variants in human cells.
Figure 5B:
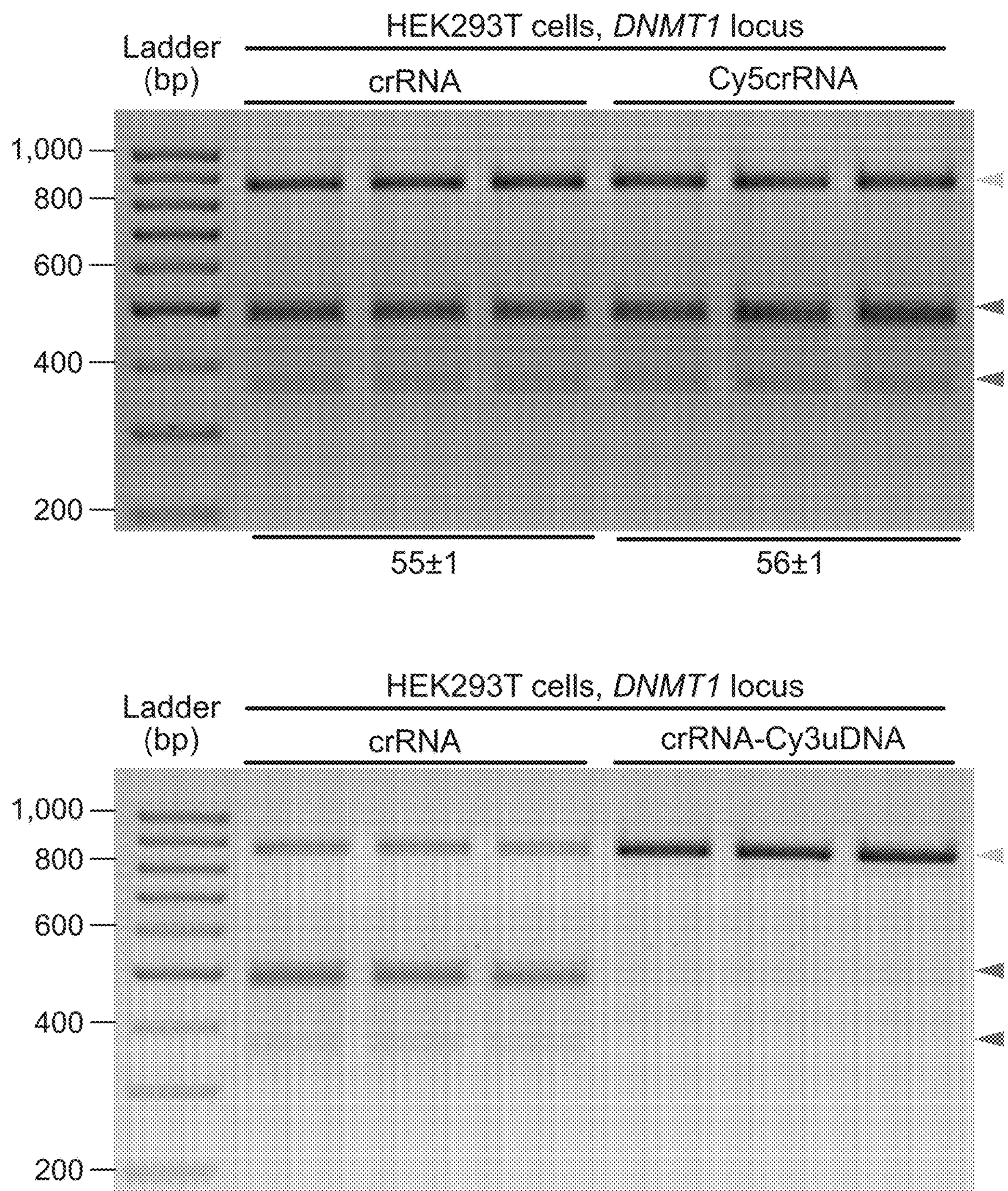
Figure 5C:
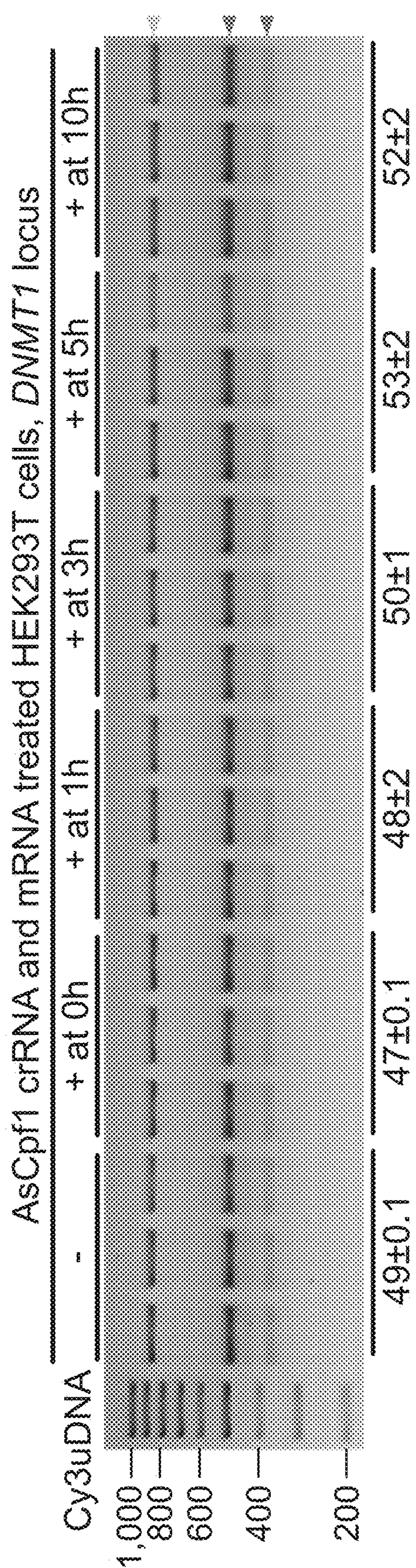
Figure 5D:
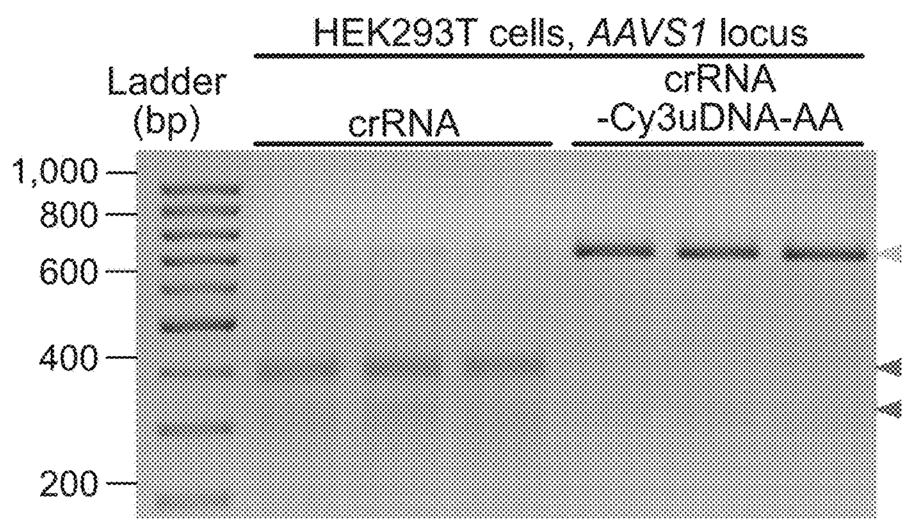
Figure 5D:
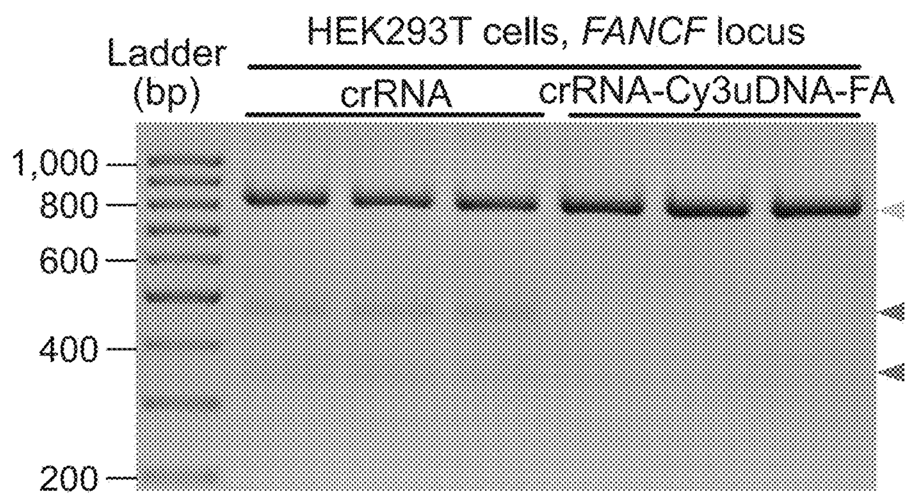
Figure 5E:
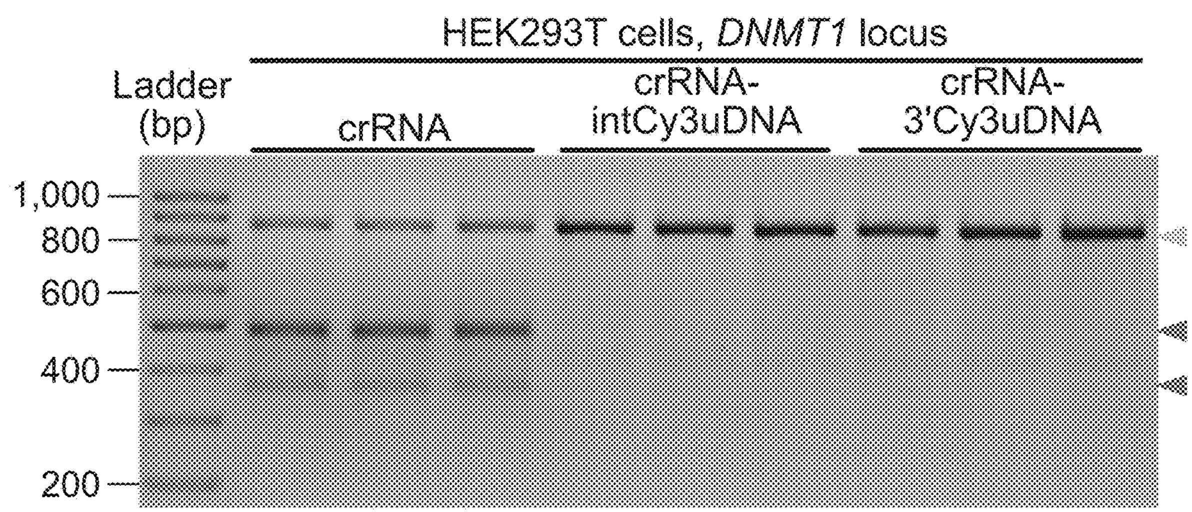

In order to differentiate different components in the Cpf1 system, the 3'-end of crRNA was labeled with a Cy5 fluorescent probe and 5'-end of the unmodified DNA oligonucleotide (termed uDNA) with a Cy3 fluorescent probe (FIG. 5*a*). The function of Cy5-labeled crRNA (Cy5crRNA) and Cy3-labeled uDNA (Cy3 uDNA, hybridized into Cy3uDNA-crRNA duplex form, FIG. 5*a*) was tested in HEK293T cells. Cy5crRNA showed equivalent activity to crRNA, while Cy3uDNA-crRNA completely lost gene cutting function (FIG. 5*b*). Similarly, neither Cy3uDNA-AAVS1 nor Cy3uDNA-FANCF in duplex form (FIG. 5*a*) was able to induce gene cleavage at the AAVS1 and FANCF locus (FIG. 5*c*). Cy3uDNA may also be an inhibitor as psDNA for the Cpf1 system and its inhibition activity in HEK293T cells was tested. However, Cy3uDNA was unable to inhibit the gene cutting activity (FIG. 5*d*). In addition, the results were the same when Cy3 was installed in the middle or at the 3'-end of uDNA (intCy3uDNA and 3'Cy3uDNA; FIG. 5*a,c*). These findings revealed that Cy5 probe was feasible to label the 3'-end of crRNA, while Cy3 probe was not suitable for labeling the complementary oligonucleotide.

In summary, chimeric crRNAs comprised of both deoxynucleotides and ribonucleotides were investigated and their gene cleavage activity was tested. Current results show that a large amount of deoxynucleotide substitutions are not applicable to gene cutting by the AsCpf1. Moreover, a series of oligonucleotides were designed in order to regulate the activity of Cpf1. Intriguingly, phosphorothioate (ps)-modified DNA oligonucleotides are effective inhibitors for Cpf1. These PS-modified DNA oligonucleotides enabled us to switch off gene cutting of both AsCpf1 and LbCpf1. Also, similar phenomenon was observed in three genomic loci. The inhibition effect is time- and dose-dependent in human cells. Further studies on the mechanism of action are needed to elucidate the regulation effects of oligonucleotides on the Cpf1 function. Overall, these results provide new tools to understand and modulate the CRISPR-Cpf1 system. In cases of acute toxic effects of the CRISPR system occur in clinical use, this strategy can serve as an important antidote.

Methods

Generation of crRNA variants. crRNAs (FIG. 3) were synthesized by TriLink™ BioTechnologies via a solid-phase DNA/RNA synthesizer, purified by polyacrylamide gel electrophoresis system, and characterized by electrospray-ionization mass spectrometry. Chimeric crRNAs (crRNA1-crRNA4, FIG. 3) were obtained from Integrated DNA Technologies by substituting the crRNA sequence with corresponding DNA sequence at the following regions: 5'-handle, guide segment or full-length wild-type crRNA. Unmodified oligonucleotides were obtained from Eurofins Genomics, and chemically modified oligonucleotides were obtained from Integrated DNA Technologies. crRNA duplexes (crRNA5-crRNA24, FIG. 3) were generated by hybridization of an equivalent molar of AsCpf1 crRNA targeting DNMT1 and the customized oligonucleotides. The mixture was heated to 95° C. for 30 s in Tris-EDTA buffer, followed by gradient cooling to room temperate at a rate of 0.1° C./s. crRNA duplexes derived from AsCpf1 crRNAs targeting AAVS and FANCF locus, and LbCpf1 crRNAs targeting DNMT1 locus were obtained through the same procedure. The sequences of all ONs used were listed in Table 1.

Gene cutting induced by crRNA variants. HEK293T or Hep3B cells (American Type Culture Collection, ATCC) were seeded in 24-well plates in medium (Dulbecco's Modified Eagle's Medium for HEK-293T cells and Eagle's Minimum Essential Medium for Hep3B cells) supplement with 10% FBS for 24 h. Cells were then treated with 38 or 114 pmol crRNA variants formulated with Lipofectamine 3000 (Life Technologies) in Opti-MEM™ I reduced serum medium following manufacturer's instructions. Meanwhile, 500 or 1500 ng of Cpf1 plasmid (generously provided by Dr. F. Zhang) or mRNA (TriLink™ BioTechnologies) were formulated with the same protocol and add to each well. Cells treated with the wild-type crRNA plus Cpf1 served as the control group.

Time- and dose-dependent inhibition of Cpf1 activity. In order to study the effects of time interval, 2.5 times molar excess of PS-modified DNA over wild-type crRNA was added to cells treated with the wild-type crRNA plus Cpf1 mRNA at different time points (0, 1, 3, 5 and 10 h). In the case of dose-dependence study, crRNA and Cpf1 mRNA-treated cells were exposed with different molar of PS-modified DNA (the molar ratio of PS-DNA:crRNA ranged from 1:6.25 to 6.25:1) at 5 hrs. In both situations, the end point was 48 h after the addition of a combination of wild-type crRNA and Cpf1 mRNA.

T7E1 enzymatic cleavage assay. Two days after treatment, genomic DNA was harvested from treated cells with the DNeasy™ Blood & Tissue Kit (QIAGEN). Polymerase chain reactions (PCRs) were then performed using Q5™ Hot-start High-Fidelity DNA Polymerase (New England Biolabs). Primers (Eurofins Genomics) flanking the targeted region were used. The PCR products were then annealed in NEBuffer 2 (50 mM NaCl, 10 mM Tris-HCl, 10 mM $MgCl_2$, 1 mM DTT, New England Biolabs) and subsequently digested by T7 Endonuclease I (T7E1, New England Biolabs) at 37° C. for 30 min. The fraction cleaved was separated on 2% agarose gels, visualized on the ChemiDoc™ MP imaging system (Bio-Rad Laboratories), and analyzed by the Image Lab 5.2 analysis software (Bio-Rad Laboratories).

REFERENCES CITED IN THIS EXAMPLE

1 Zetsche, B. et al. Cpf1 is a single RNA-guided endonuclease of a class 2 CRISPR-Cas system. *Cell* 163, 759-771, doi: 10.1016/j.cell.2015.09.038 (2015).

2 Yamano, T. et al. Crystal Structure of Cpf1 in Complex with Guide RNA and Target DNA. *Cell* 165, 949-962, doi: 10.1016/j.cell.2016.04.003 (2016).

3 Fonfara, I., Richter, H., Bratovic, M., Le Rhun, A. & Charpentier, E. The CRISPR-associated DNA-cleaving enzyme Cpf1 also processes precursor CRISPR RNA. *Nature* 532, 517-521, doi: 10.1038/nature17945 (2016).

4 Dong, D. et al. The crystal structure of Cpf1 in complex with CRISPR RNA. *Nature* 532, 522-526, doi: 10.1038/nature 17944 (2016).

5 Gao, P., Yang, H., Rajashankar, K. R., Huang, Z. & Patel, D. J. Type V CRISPR-Cas Cpf1 endonuclease employs a unique mechanism for crRNA-mediated target DNA recognition. Cell research 26, 901-913, doi: 10.1038/cr.2016.88 (2016).

6 Swarts, D. C., van der Oost, J. & Jinek, M. Structural Basis for Guide RNA Processing and Seed-Dependent DNA Targeting by CRISPR-Cas12a. Molecular cell 66, 221-233 e224, doi: 10.1016/j.molcel.2017.03.016 (2017).

7 Stella, S., Alcon, P. & Montoya, G. Structure Of The Cpf1 Endonuclease R-Loop Complex After Target DNA Cleavage. bioRxiv, doi: 10.1101/122648 (2017).

8 Kim, Y. et al. Generation of knockout mice by Cpf1-mediated gene targeting. *Nature biotechnology* 34, 808-810, doi: 10.1038/nbt.3614 (2016).

9 Zetsche, B. et al. Multiplex gene editing by CRISPR-Cpf1 using a single crRNA array. *Nature biotechnology* 35, 31-34, doi: 10.1038/nbt.3737 (2017).

10 Begemann, M. B. et al. *Precise insertion and guided editing of higher plant genomes using Cpf*1 *CRISPR nucleases. bioRxiv*, doi: 10.1101/109983 (2017).

11 Zhang, Y. et al. CRISPR-Cpf1 correction of muscular dystrophy mutations in human cardiomyocytes and mice. Science Advances 3, doi: 10.1126/sciadv.1602814 (2017).

12 Hur, J. K. et al. Targeted mutagenesis in mice by electroporation of Cpf1 ribonucleoproteins. *Nature biotechnology* 34, 807-808, doi: 10.1038/nbt.3596 (2016).

13 Kim, H. et al. CRISPR/Cpf1-mediated DNA-free plant genome editing. Nature communications 8, 14406, doi: 10.1038/ncomms14406 (2017).

14 Yin, X. et al. CRISPR-Cas9 and CRISPR-Cpf1 mediated targeting of a stomatal developmental gene EPFL9 in rice. *Plant cell reports* 36, 745-757, doi: 10.1007/s00299-017-2118-z (2017).

15 Tang, X. et al. A CRISPR-Cpf1 system for efficient genome editing and transcriptional repression in plants. Nature plants 3, 17018, doi: 10.1038/nplants.2017.18 (2017).

16 Endo, A., Masafumi, M., Kaya, H. & Toki, S. Efficient targeted mutagenesis of rice and tobacco genomes using Cpf1 from *Francisella novicida*. Scientific reports 6, 38169, doi: 10.1038/srep38169 (2016).

17 Xu, R. et al. Generation of targeted mutant rice using a CRISPR-Cpf1 system. *Plant biotechnology journal* 15, 713-717, doi: 10.1111/pbi.12669 (2017).

18 Wang, M., Mao, Y., Lu, Y., Tao, X. & Zhu, J. K. Multiplex Gene Editing in Rice Using the CRISPR-Cpf1 System. Molecular plant, doi: 10.1016/j.molp.2017.03.001 (2017).

19 Bosley, K. S. et al. CRISPR germline engineering—the community speaks. *Nature biotechnology* 33, 478-486, doi: 10.1038/nbt.3227 (2015).

20 Latorre, A., Latorre, A. & Somoza, A. Modified RNAs in CRISPR/Cas9: An Old Trick Works Again. *Angewandte Chemie* 55, 3548-3550, doi: 10.1002/anie.201512002 (2016).

21 Li, B. et al. Engineering CRISPR-Cpf1 crRNAs and mRNAs to maximize genome editing efficiency. *Nature Biomedical Engineering* 1, 0066 (2017).

22 Dang, Y. et al. Optimizing sgRNA structure to improve CRISPR-Cas9 knockout efficiency. Genome biology 16, 280, doi: 10.1186/s13059-015-0846-3 (2015).

23 Pawluk, A. et al. Naturally Occurring Off-Switches for CRISPR-Cas9. *Cell* 167, 1829-1838 e1829, doi: 10.1016/j.cell.2016.11.017 (2016).

24 Rauch, B. J. et al. Inhibition of CRISPR-Cas9 with Bacteriophage Proteins. *Cell* 168, 150-158 e110, doi: 10.1016/j.cell.2016.12.009 (2017).

25 Nunez, J. K., Harrington, L. B. & Doudna, J. A. Chemical and Biophysical Modulation of Cas9 for Tunable Genome Engineering. ACS chemical biology 11, 681-688, doi: 10.1021/acschembio.5b01019 (2016).

26 Richter, F. et al. Switchable Cas9. *Current opinion in biotechnology* 48, 119-126, doi:10.1016/j.copbio.2017.03.025 (2017).

27 Juliano, R. L. The delivery of therapeutic oligonucleotides. Nucleic acids research 44, 6518-6548, doi: 10.1093/nar/gkw236 (2016).

28 Kim, D. et al. Genome-wide analysis reveals specificities of Cpf1 endonucleases in human cells. *Nature biotechnology* 34, 863-868, doi: 10.1038/nbt.3609 (2016).

29 Kleinstiver, B. P. et al. Genome-wide specificities of CRISPR-Cas Cpf1 nucleases in human cells. *Nature biotechnology* 34, 869-874, doi: 10.1038/nbt.3620 (2016).

TABLE 1 crRNAs and oligonucleotides

| Name of oligonucleotides | Length (nt) | Sequence (5' to 3') |
|---|---|---|
| crRNA targeting DNMT1 | 43 | UAAUUUCUACUCUUGUAGAUCUGAUGGUCCAUGUCUGUUACUC (SEQ ID NO: 3) |
| Oligo 1 (crRNA1) | 43 | TAATTTCTACTCTTGTAGATCTGATGGTCCATGTCTGTTACTC (SEQ ID NO: 4) |
| Oligo 2 (crRNA2) | 43 | TAATTTCTACTCTTGTAGAUCUGAUGGUCCAUGUCUGUUACUC (SEQ ID NO: 5) |
| Oligo 3 (crRNA3) | 43 | UAAUUUCUACUCUUGUAGAUCTGATGGTCCATGTCTGTTACTC (SEQ ID NO: 6) |
| Oligo 4 (crRNA4) | 43 | UAAUTTCUACUCTTGTAGAUCUGAUGGUCCATGUCUGUTACTC (SEQ ID NO: 7) |
| Oligo 5 (crRNA5) | 29 | GAGTAACAGACATGGACCATCAGAAATTA (SEQ ID NO: 8) |
| Oligo 6 (uDNA) | 43 | GAGTAACAGACATGGACCATCAGATCTACAAGAGTAGAAATTA (SEQ ID NO: 9) |
| Oligo 7 | 20 | ATCTACAAGAGTAGAAATTA (SEQ ID NO: 10) |
| Oligo 8 | 10 | GTAGAAATTA (SEQ ID NO: 11) |
| Oligo 9 | 10 | ATCTACAAGA (SEQ ID NO: 12) |
| Oligo 10 | 23 | GAGTAACAGACATGGACCATCAG (SEQ ID NO: 13) |
| Oligo 11 | 10 | GGACCATCAG (SEQ ID NO: 14) |
| Oligo 12 | 13 | GAGTAACAGACAT (SEQ ID NO: 15) |
| Oligo 13 | 20 | TAACAGACATGGACCATCAG (SEQ ID NO: 16) |
| Oligo 14 | 10 | TAACAGACAT (SEQ ID NO: 17) |
| Oligo 15 (ps42DNA) | 43 | **GAGTAACAGACATGGACCATCAGATCTACAAGAGTAGAAATTA** (SEQ ID NO: 18) |
| Oligo 16 | 20 | **ATCTACAAGAGTAGAAATTA** (SEQ ID NO: 19) |
| Oligo 17 | 23 | **GAGTAACAGACATGGACCATCAG** (SEQ ID NO: 20) |
| Oligo 18 | 43 | GAGUAACAGACAUGGACCAUCAGAUCUACAAGAGUAGAAAUUA (SEQ ID NO: 21) |
| Oligo 19 | 20 | AUCUACAAGAGUAGAAAUUA (SEQ ID NO: 22) |
| Oligo 20 | 13 | GAGUAACAGACAU (SEQ ID NO: 23) |

TABLE 1-continued

| crRNAs and oligonucleotides | | |
|---|---|---|
| Name of oligonucleotides | Length (nt) | Sequence (5' to 3') |
| Oligo 21 | 20 | *AUCUACAAGAGUAGAAAUUA* (SEQ ID NO: 24) |
| Oligo 22 | 13 | *GAGUAACAGACAU* (SEQ ID NO: 25) |
| Oligo 23 | 20 | AUCUACAAGAGUAGAAAUUA (SEQ ID NO: 34) |
| Oligo 24 | 13 | GAGUAACAGACAU (SEQ ID NO: 26) |
| Oligo 25 | 5 | GAGUA (SEQ ID NO: 27) |
| crRNA targeting AAVS | 43 | UAAUUUCUACUCUUGUAGAUCUUACGAUGGAGCCAGAGAGGAU (SEQ ID NO: 28) |
| ps42DNA-AAVS1 | 43 | **ATCCTCTCTGGCTCCATCGTAAGATCTACAAGAGTAGAAATTA** (SEQ ID NO: 29) |
| crRNA targeting FANCF | 43 | UAAUUUCUACUCUUGUAGAUGUCGGCAUGGCCCCAUUCGCACG (SEQ ID NO: 30) |
| ps42DNA-FANCF | 43 | **CGTGCGAATGGGGCCATGCCGACATCTACAAGAGTAGAAATTA** (SEQ ID NO: 31) |
| LbcrRNA targeting DNMT1 | 43 | AAUUUCUACUAAGUGUAGAUCUGAUGGUCCAUGUCUGUUACUC (SEQ ID NO: 32) |
| Lbps42DNA | 43 | **GAGTAACAGACATGGACCATCAGATCTACAAGAGTAGAAATTA** (SEQ ID NO: 33) |

Unmodified RNA base is shown with underlined text.
Unmodified DNA base is shown with unmodified text.
PS-linkage modified DNA is shown with bold text.
2'-fluoro modified RNA is shown with italicized text.
2'-O-methyl modified RNA is shown with double-underlined text.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method for inhibiting a CRISPR genome editing system in a cell comprising:

contacting the cell with a CRISPR genome editing system, wherein the system comprises a guide RNA and a nuclease;

contacting the cell with a chemically modified nucleic acid comprising SEQ ID NO: 18, and wherein all nucleotides in the chemically modified nucleic acid are phosphorothioate (PS);

wherein the nuclease is a Cpf1 protein;

wherein the chemically modified nucleic acid is complementary to the guide RNA;

wherein the chemically modified nucleic acid inhibits the activity of the nuclease of the CRISPR genome editing system.

2. The method of claim 1, wherein the complementary region between the nucleic acid and the guide RNA comprises at least 10 nucleotides.

3. The method of claim 1, wherein the chemically modified nucleic acid is RNA or DNA.

* * * * *

SEQUENCE LISTING

```
Sequence total quantity: 34
SEQ ID NO: 1            moltype = DNA  length = 4020
FEATURE                 Location/Qualifiers
misc_feature            1..4020
                        note = Synthetic Construct
source                  1..4020
                        mol_type = other DNA
                        organism = synthetic construct
SEQUENCE: 1
atggccccaa agaagaagcg gaaggtcggt atccacggag tcccagcagc cacacagttc  60
gagggcttta ccaacctgta tcaggtgagc aagacactgc ggtttgagct gatcccacag  120
ggcaagaccc tgaagcacat ccaggagcag ggcttcatcg aggaggacaa ggcccgcaat  180
gatcactaca aggagctgaa gcccatcatc gatcggatct acaagaccta tgccgaccag  240
tgcctgcagc tggtgcagct ggattgggag aacctgagcg ccgccatcga ctcctataga  300
aaggagaaaa ccgaggagac aaggaacgcc ctgatcgagg agcaggccac atatcgcaat  360
gccatccacg actacttcat cggccggaca gacaacctga ccgatgccat caataagaga  420
cacgccgaga tctacaaggg cctgttcaag gccgagctgt ttaatggcaa ggtgctgaag  480
cagctgggca ccgtgaccac aaccgagcac gagaacgccc tgctgcggag cttcgacaag  540
tttacaacct acttctccgg cttttatgag aacaggaaga acgtgttcag cgccgaggat  600
```

```
atcagcacag ccatcccaca ccgcatcgtg caggacaact tccccaagtt taaggagaat  660
tgtcacatct tcacacgcct gatcaccgcc gtgcccagcc tgcgggagca ctttgagaac  720
gtgaagaagg ccatcggcat cttcgtgagc acctccatcg aggaggtgtt ttccttccct  780
ttttataacc agctgctgac acagacccag atcgacctgt ataaccagct gctgggagga  840
atctctcggg aggcaggcac cgagaagatc aagggcctga acgaggtgct gaatctggcc  900
atccagaaga atgatgagac agcccacatc atcgcctccc tgccacacag attcatcccc  960
ctgtttaagc agatcctgtc cgataggaac accctgtctt tcatcctgga ggagtttaag  1020
agcgacgagg aagtgatcca gtccttctgc aagtacaaga cactgctgag aaacgagaac  1080
gtgctggaga cagccgaggc cctgtttaac gagctgaaca gcatcgacct gacacacatc  1140
ttcatcagcc acaagaagct ggagacaatc agcagcgccc tgtgcgacca ctgggataca  1200
ctgaggaatg ccctgtatga gcggagaatc tccgagctga caggcaagat caccaagtct  1260
gccaaggaga aggtgcagcg cagcctgaag cacgaggata tcaacctgca ggagatcatc  1320
tctgccgcag gcaaggagct gagcgaggcc ttcaagcaga aaaccagcga gatcctgtcc  1380
cacgcacacg ccgccctgga tcagccactg cctacaaccc tgaagaagca ggaggagaag  1440
gagatcctga agtctcagct ggacagcctg ctgggcctgt accacctgct ggactggttt  1500
gccgtggatg agtccaacga ggtggacccc gagttctctg cccggctgac cggcatcaag  1560
ctggagatgg agccttctct gagcttctac aacaaggcca gaaattatgc caccaagaag  1620
ccctactccg tggagaagtt caagctgaac tttcagatgc ctacactggc ctctggctgg  1680
gacgtgaata aggagaagaa caatggcgcc atcctgtttg tgaagaacgg cctgtactat  1740
ctgggcatca tgccaaagca gaagggcagg tataaggccc tgagcttcga gcccacagag  1800
aaaaccagcg agggctttga taagatgtac tatgactact tccctgatgc cgccaagatg  1860
atcccaaagt gcagcaccca gctgaaggcc gtgacagccc actttcagac ccacacaacc  1920
cccatcctgc tgtccaacaa tttcatcgag cctctggaga tcacaaagga gatctacgac  1980
ctgaacaatc ctgagaagga gccaaagaag tttcagacag cctacgccaa gaaaaccggc  2040
gaccagaagg gctacagaga ggccctgtgc aagtggatcg acttcacaag ggattttctg  2100
tccaagtata ccaagacaac ctctatcgat ctgtctagcc tgcggccatc ctctcagtat  2160
aaggacctgg gcgagtacta tgccgagctg aatcccctgc tgtaccacat cagcttccag  2220
agaatcgccg agaaggagat catggatgcc gtggagacag gcaagctgta cctgttccag  2280
atctataaca aggactttgc caagggccac cacggcaagc ctaatctgca cacactgtat  2340
tggaccggcc tgttttctcc agagaacctg gccaagacaa gcatcaagct gaatggccag  2400
gccgagctgt tctaccgccc taagtccagg atgaagagga tggcacaccg gctgggagag  2460
aagatgctga acaagaagct gaaggatcag aaaaccccaa tccccgacac cctgtaccag  2520
gagctgtacg actatgtgaa tcacagactg tcccacgacc tgtctgatga ggccagggcc  2580
ctgctgccca acgtgatcac caaggaggtg tctcacgaga tcatcaagga taggcgcttt  2640
accagcgaca agttcttttt ccacgtgcct atcacactga actatcaggc cgccaattcc  2700
ccatctaagt tcaaccagag ggtgaatgcc tacctgaagg agcaccccga gacacctatc  2760
atcggcatcg atcggggcga gagaaacctg atctatatca cagtgatcga ctccaccggc  2820
aagatcctgg agcagcggag cctgaacacc atccagcagt ttgattacca gaagaagctg  2880
gacaacaggg agaaggagag ggtggcagca aggcaggcct ggtctgtggt gggcacaatc  2940
aaggatctga agcagggcta tctgagccag gtcatccacg agatcgtgga cctgatgatc  3000
cactaccagg ccgtggtggt gctggagaac ctgaatttcg gctttaagag caagaggacc  3060
ggcatcgccg agaaggccgt gtaccagcag ttcgagaaga tgctgatcga taagctgaat  3120
tgcctggtgc tgaaggacta tccagcagag aaagtgggag gcgtgctgaa cccataccag  3180
ctgacagacc agttcacctc ctttgccaag atgggcaccc agtctggctt cctgttttac  3240
gtgcctgccc catatacatc taagatcgat cccctgaccg gcttcgtgga cccccttcgtg  3300
tggaaaacca tcaagaatca cgagagccgc aagcacttcc tggagggctt cgactttctg  3360
cactacgacg tgaaaaccgg cgacttcatc ctgcacttta agatgaacag aaatctgtcc  3420
ttccagaggg gcctgcccgg ctttatgcct gcatgggata tcgtgttcga gaagaacgag  3480
acacagtttg acgccaaggg cacccctttc atcgccggca agagaatcgt gccagtgatc  3540
gagaatcaca gattcaccgg cagataccgg gacctgtatc ctgccaacga gctgatcgcc  3600
ctgctggagg agaagggcat cgtgttcagg gatggctcca acatcctgcc aaagctgctg  3660
gagaatgacg attctcacgc catcgacacc atggtggccc tgatccgcag cgtgctgcag  3720
atgcggaact ccaatgccgc cacaggcgag gactatatca acagccccgt gcgcgatctg  3780
aatggcgtgt gcttcgactc ccggtttcag aacccagagt ggcccatgga cgccgatgcc  3840
aatggcgcct accacatcgc cctgaagggc cagctgctgc tgaatcacct gaaggagagc  3900
aaggatctga agctgcagaa cggcatctcc aatcaggact ggctggccta catccaggag  3960
ctgcgcaaca agcgtcctgc tgctactaag aaagctggtc aagctaagaa aaagaaataa  4020

SEQ ID NO: 2           moltype = DNA  length = 3783
FEATURE                Location/Qualifiers
misc_feature           1..3783
                       note = Synthetic Construct
source                 1..3783
                       mol_type = other DNA
                       organism = synthetic construct
SEQUENCE: 2
atggccccaa agaagaagcg gaaggtcggt atccacggag tcccagcagc cagcaagctg  60
gagaagttta caaactgcta ctccctgtct aagaccctga ggttcaaggc catccctgtg  120
ggcaagaccc aggagaacat cgacaataag cggctgctgg tggaggacga gaagagagcc  180
gaggattata agggcgtgaa gaagctgctg gatcgctact atctgtcttt tatcaacgac  240
gtgctgcaca gcatcaagct gaagaatctg aacaattaca tcagcctgtt ccggaagaaa  300
accagaaccg agaaggagaa taaggagctg gagaacctgg agatcaatct gcggaaggag  360
atcgccaagg ccttcaaggg caacgagggc tacaagtccc tgtttaagaa ggatatcatc  420
gagacaatcc tgccagagtt cctggacgat aaggacgaga tcgccctggt gaacagcttc  480
aatggcttta ccacagcctt caccggcttc tttgataaca gagagaatat gttttccgag  540
gaggccaaga gcacatccat cgccttcagg tgtatcaacg agaatctgac ccgctacatc  600
tctaatatgg acatcttcga gaaggtggac gccatctttg ataagcacga ggtgcaggag  660
atcaaggaga agatcctgaa cagcgactat gatgtggagg atttctttga gggcgagttc  720
tttaactttg tgctgacaca ggagggcatc gacgtgtata acgccatcat cggcggcttc  780
```

```
gtgaccgaga gcggcgagaa gatcaagggc ctgaacgagt acatcaacct gtataatcag  840
aaaaccaagc agaagctgcc taagtttaag ccactgtata agcaggtgct gagcgatcgg  900
gagtctctga gcttctacgg cgagggctat acatccgatg aggaggtgct ggaggtgttt  960
agaaacaccc tgaacaagaa cagcgagatc ttcagctcca tcaagaagct ggagaagctg  1020
ttcaagaatt ttgacgagta ctctagcgcc ggcatctttg tgaagaacgg ccccgccatc  1080
agcacaatct ccaaggatat cttcggcgag tggaacgtga tccgggacaa gtggaatgcc  1140
gagtatgacg atatccacct gaagaagaag gccgtggtga ccgagaagta cgaggacgat  1200
cggagaaagt ccttcaagaa gatcggctcc ttttctctgg agcagctgca ggagtacgcc  1260
gacgccgatc tgtctgtggt ggagaagctg aaggagatca tcatccagaa ggtggatgag  1320
atctacaagg tgtatggctc ctctgagaag ctgttcgacg ccgattttgt gctggagaag  1380
agcctgaaga agaacgacgc cgtggtggcc atcatgaagg acctgctgga ttctgtgaag  1440
agcttcgaga attacatcaa ggccttcttt ggcgagggca aggagacaaa cagggacgag  1500
tccttctatg gcgattttgt gctggcctac gacatcctgc tgaaggtgga ccacatctac  1560
gatgccatcc gcaattatgt gacccagaag ccctactcta aggataagtt caagctgtat  1620
tttcagaacc ctcagttcat gggcggctgg gacaaggata aggagacaga ctatcgggcc  1680
accatcctga gatacggctc caagtactat ctggccatca tggataagaa gtacgccaag  1740
tgcctgcaga agatcgacaa ggacgatgtg aacggcaatt acgagaagat caactataag  1800
ctgctgcccg gccctaataa gatgctgcca aaggtgttct tttctaagaa gtggatggcc  1860
tactataacc ccagcgagga catccagaag atctacaaga atggcacatt caagaagggc  1920
gatatgttta acctgaatga ctgtcacaag ctgatcgact tctttaagga tagcatctcc  1980
cggtatccaa agtggtccaa tgcctacgat ttcaactttt ctgagacaga gaagtataag  2040
gacatcgccg gcttttacag agaggtggag gagcagggct ataaggtgag cttcgagtct  2100
gccagcaaga aggaggtgga taagctggtg gaggagggca agctgtatat gttccagatc  2160
tataacaagg acttttccga taagtctcac ggcacaccca atctgcacac catgtacttc  2220
aagctgctgt ttgacgagaa caatcacgga cagatcaggc tgagcggagg agcagagctg  2280
ttcatgaggc gcgcctccct gaagaaggag gagctggtgg tgcacccagc caactcccct  2340
atcgccaaca agaatccaga taatcccaag aaaaccacaa ccctgtccta cgacgtgtat  2400
aaggataaga ggttttctga ggaccagtac gagctgcaca tcccaatcgc catcaataag  2460
tgccccaaga acatcttcaa gatcaataca gaggtgcgcg tgctgctgaa gcacgacgat  2520
aacccctatg tgatcggcat cgatagggc gagcgcaatc tgctgtatat cgtggtggtg  2580
gacggcaagg gcaacatcgt ggagcagtat tccctgaacg agatcatcaa caacttcaac  2640
ggcatcagga tcaagacaga ttaccactct ctgctggaca agaaggagaa ggagaggttc  2700
gaggcccgcc agaactggac ctccatcgag aatatcaagg agctgaaggc cggctatatc  2760
tctcaggtgg tgcacaagat ctgcgagctg gtggagaagt acgatgccgt gatcgccctg  2820
gaggacctga actctggctt taagaatagc cgcgtgaagg tggagaagca ggtgtatcag  2880
aagttcgaga agatgctgat cgataagctg aactacatgg tggacaagaa gtctaatcct  2940
tgtgcaacag gcggcgccct gaagggctat cagatcacca ataagttcga gagctttaag  3000
tccatgtcta cccagaacgg cttcatcttt tacatccctg cctggctgac atccaagatc  3060
gatccatcta ccggctttgt gaacctgctg aaaaccaagt ataccagcat cgccgattcc  3120
aagaagttca tcagctcctt tgacaggatc atgtacgtgc ccgaggagga tctgttcgag  3180
tttgccctgg actataagaa cttctctcgc acagacgccg attacatcaa gaagtggaag  3240
ctgtactcct acggcaaccg gatcagaatc ttccggaatc ctaagaagaa caacgtgttc  3300
gactgggagg aggtgtgcct gaccagcgcc tataaggagc tgttcaacaa gtacggcatc  3360
aattatcagc agggcgatat cagagccctg ctgtgcgagc agtccgacaa ggccttctac  3420
tctagcttta tggccctgat gagcctgatg ctgcagatgc ggaacagcat cacaggccgc  3480
accgacgtgg attttctgat cagccctgtg aagaactccg acggcatctt ctacgatagc  3540
cggaactatg aggcccagga gaatgccatc ctgccaaaga acgccgacgc caatggcgcc  3600
tataacatcg ccagaaaggt gctgtgggcc atcggccagt tcaagaaggc cgaggacgag  3660
aagctggata aggtgaagat cgccatctct aacaaggagt ggctggagta cgcccagacc  3720
agcgtgaagc acaagcgtcc tgctgctact aagaaagctg gtcaagctaa gaaaaagaaa  3780
taa                                                                3783

SEQ ID NO: 3           moltype = RNA  length = 43
FEATURE                Location/Qualifiers
misc_feature           1..43
                       note = Synthetic Construct
source                 1..43
                       mol_type = other RNA
                       organism = synthetic construct
SEQUENCE: 3
taatttctac tcttgtagat ctgatggtcc atgtctgtta ctc                   43

SEQ ID NO: 4           moltype = RNA  length = 43
FEATURE                Location/Qualifiers
source                 1..43
                       mol_type = other RNA
                       organism = synthetic construct
modified_base          1..43
                       mod_base = OTHER
                       note = T is thymine
SEQUENCE: 4
taatttctac tcttgtagat ctgatggtcc atgtctgtta ctc                   43

SEQ ID NO: 5           moltype = RNA  length = 43
FEATURE                Location/Qualifiers
source                 1..43
                       mol_type = other RNA
                       organism = synthetic construct
modified_base          1..17
```

```
                      mod_base = OTHER
                      note = Wherever T is thymine
SEQUENCE: 5
taatttctac tcttgtagat ctgatggtcc atgtctgtta ctc                    43

SEQ ID NO: 6          moltype = RNA  length = 43
FEATURE               Location/Qualifiers
source                1..43
                      mol_type = other RNA
                      organism = synthetic construct
modified_base         22..43
                      mod_base = OTHER
                      note = whereever T is Thymine
SEQUENCE: 6
taatttctac tcttgtagat ctgatggtcc atgtctgtta ctc                    43

SEQ ID NO: 7          moltype = RNA  length = 43
FEATURE               Location/Qualifiers
source                1..43
                      mol_type = other RNA
                      organism = synthetic construct
modified_base         5..6
                      mod_base = OTHER
                      note = T is thymine
modified_base         13..14
                      mod_base = OTHER
                      note = T is thymine
modified_base         16
                      mod_base = OTHER
                      note = T is thymine
modified_base         32
                      mod_base = OTHER
                      note = T is thymine
modified_base         39
                      mod_base = OTHER
                      note = T is thymine
modified_base         42
                      mod_base = OTHER
                      note = T is thymine
SEQUENCE: 7
taatttctac tcttgtagat ctgatggtcc atgtctgtta ctc                    43

SEQ ID NO: 8          moltype = RNA  length = 29
FEATURE               Location/Qualifiers
source                1..29
                      mol_type = other RNA
                      organism = synthetic construct
modified_base         1..29
                      mod_base = OTHER
                      note = wherever T is thymine
SEQUENCE: 8
gagtaacaga catggaccat cagaaatta                                    29

SEQ ID NO: 9          moltype = DNA  length = 43
FEATURE               Location/Qualifiers
misc_feature          1..43
                      note = Synthetic Construct
source                1..43
                      mol_type = other DNA
                      organism = synthetic construct
SEQUENCE: 9
gagtaacaga catggaccat cagatctaca agagtagaaa tta                    43

SEQ ID NO: 10         moltype = DNA  length = 20
FEATURE               Location/Qualifiers
misc_feature          1..20
                      note = Synthetic Construct
source                1..20
                      mol_type = other DNA
                      organism = synthetic construct
SEQUENCE: 10
atctacaaga gtagaaatta                                              20

SEQ ID NO: 11         moltype = DNA  length = 10
FEATURE               Location/Qualifiers
misc_feature          1..10
                      note = Synthetic Construct
source                1..10
                      mol_type = other DNA
```

```
                        organism = synthetic construct
SEQUENCE: 11
gtagaaatta                                                        10

SEQ ID NO: 12           moltype = DNA  length = 10
FEATURE                 Location/Qualifiers
misc_feature            1..10
                        note = Synthetic Construct
source                  1..10
                        mol_type = other DNA
                        organism = synthetic construct
SEQUENCE: 12
atctacaaga                                                        10

SEQ ID NO: 13           moltype = DNA  length = 23
FEATURE                 Location/Qualifiers
misc_feature            1..23
                        note = Synthetic Construct
source                  1..23
                        mol_type = other DNA
                        organism = synthetic construct
SEQUENCE: 13
gagtaacaga catggaccat cag                                         23

SEQ ID NO: 14           moltype = DNA  length = 10
FEATURE                 Location/Qualifiers
misc_feature            1..10
                        note = Synthetic Construct
source                  1..10
                        mol_type = other DNA
                        organism = synthetic construct
SEQUENCE: 14
ggaccatcag                                                        10

SEQ ID NO: 15           moltype = DNA  length = 13
FEATURE                 Location/Qualifiers
misc_feature            1..13
                        note = Synthetic Construct
source                  1..13
                        mol_type = other DNA
                        organism = synthetic construct
SEQUENCE: 15
gagtaacaga cat                                                    13

SEQ ID NO: 16           moltype = DNA  length = 20
FEATURE                 Location/Qualifiers
misc_feature            1..20
                        note = Synthetic Construct
source                  1..20
                        mol_type = other DNA
                        organism = synthetic construct
SEQUENCE: 16
taacagacat ggaccatcag                                             20

SEQ ID NO: 17           moltype = DNA  length = 10
FEATURE                 Location/Qualifiers
misc_feature            1..10
                        note = Synthetic Construct
source                  1..10
                        mol_type = other DNA
                        organism = synthetic construct
SEQUENCE: 17
taacagacat                                                        10

SEQ ID NO: 18           moltype = DNA  length = 43
FEATURE                 Location/Qualifiers
source                  1..43
                        mol_type = other DNA
                        organism = synthetic construct
modified_base           1..43
                        mod_base = OTHER
                        note = phosphodiester linkage is phosphorothioate
SEQUENCE: 18
gagtaacaga catggaccat cagatctaca agagtagaaa tta                   43

SEQ ID NO: 19           moltype = DNA  length = 20
FEATURE                 Location/Qualifiers
source                  1..20
                        mol_type = other DNA
```

```
                        organism = synthetic construct
modified_base           1..20
                        mod_base = OTHER
                        note = phosphodiester linkage is phosphorothioate
SEQUENCE: 19
atctacaaga gtagaaatta                                          20

SEQ ID NO: 20           moltype = DNA  length = 23
FEATURE                 Location/Qualifiers
modified_base           1..23
                        mod_base = OTHER
                        note = phosphodiester linkage is phosphorothioate
source                  1..23
                        mol_type = other DNA
                        organism = synthetic construct
SEQUENCE: 20
gagtaacaga catggaccat cag                                      23

SEQ ID NO: 21           moltype = RNA  length = 43
FEATURE                 Location/Qualifiers
misc_feature            1..43
                        note = Synthetic Construct
source                  1..43
                        mol_type = other RNA
                        organism = synthetic construct
SEQUENCE: 21
gagtaacaga catggaccat cagatctaca agagtagaaa tta                43

SEQ ID NO: 22           moltype = RNA  length = 20
FEATURE                 Location/Qualifiers
misc_feature            1..20
                        note = Synthetic Construct
source                  1..20
                        mol_type = other RNA
                        organism = synthetic construct
SEQUENCE: 22
atctacaaga gtagaaatta                                          20

SEQ ID NO: 23           moltype = RNA  length = 13
FEATURE                 Location/Qualifiers
misc_feature            1..13
                        note = Synthetic Construct
source                  1..13
                        mol_type = other RNA
                        organism = synthetic construct
SEQUENCE: 23
gagtaacaga cat                                                 13

SEQ ID NO: 24           moltype = RNA  length = 20
FEATURE                 Location/Qualifiers
misc_feature            1..20
                        note = Synthetic Construct
modified_base           1..20
                        mod_base = OTHER
                        note = 2'-fluoro ribose
source                  1..20
                        mol_type = other RNA
                        organism = synthetic construct
SEQUENCE: 24
atctacaaga gtagaaatta                                          20

SEQ ID NO: 25           moltype = RNA  length = 13
FEATURE                 Location/Qualifiers
misc_feature            1..13
                        note = Synthetic Construct
modified_base           1..13
                        mod_base = OTHER
                        note = 2'-fluoro ribose
source                  1..13
                        mol_type = other RNA
                        organism = synthetic construct
SEQUENCE: 25
gagtaacaga cat                                                 13

SEQ ID NO: 26           moltype = RNA  length = 13
FEATURE                 Location/Qualifiers
misc_feature            1..13
                        note = Synthetic Construct
modified_base           1..13
```

```
                        mod_base = OTHER
                        note = 2'-O-methyl ribose
source                  1..13
                        mol_type = other RNA
                        organism = synthetic construct
SEQUENCE: 26
gagtaacaga cat                                              13

SEQ ID NO: 27           moltype = RNA  length = 43
FEATURE                 Location/Qualifiers
misc_feature            1..43
                        note = Synthetic Construct
source                  1..43
                        mol_type = other RNA
                        organism = synthetic construct
SEQUENCE: 27
taatttctac tcttgtagat cttacgatgg agccagagag gat             43

SEQ ID NO: 28           moltype = DNA  length = 43
FEATURE                 Location/Qualifiers
misc_feature            1..43
                        note = Synthetic Construct
modified_base           1..43
                        mod_base = OTHER
                        note = phosphodiester linkage is phosphorothioate
source                  1..43
                        mol_type = other DNA
                        organism = synthetic construct
SEQUENCE: 28
atcctctctg gctccatcgt aagatctaca agagtagaaa tta             43

SEQ ID NO: 29           moltype = RNA  length = 43
FEATURE                 Location/Qualifiers
misc_feature            1..43
                        note = Synthetic Construct
source                  1..43
                        mol_type = other RNA
                        organism = synthetic construct
SEQUENCE: 29
taatttctac tcttgtagat gtcggcatgg ccccattcgc acg             43

SEQ ID NO: 30           moltype = DNA  length = 43
FEATURE                 Location/Qualifiers
misc_feature            1..43
                        note = Synthetic Construct
modified_base           1..43
                        mod_base = OTHER
                        note = phosphodiester linkage is phosphorothioate
source                  1..43
                        mol_type = other DNA
                        organism = synthetic construct
SEQUENCE: 30
cgtgcgaatg gggccatgcc gacatctaca agagtagaaa tta             43

SEQ ID NO: 31           moltype = RNA  length = 43
FEATURE                 Location/Qualifiers
misc_feature            1..43
                        note = Synthetic Construct
source                  1..43
                        mol_type = other RNA
                        organism = synthetic construct
SEQUENCE: 31
aatttctact aagtgtagat ctgatggtcc atgtctgtta ctc             43

SEQ ID NO: 32           moltype = DNA  length = 43
FEATURE                 Location/Qualifiers
misc_feature            1..43
                        note = Synthetic Construct
modified_base           1..43
                        mod_base = OTHER
                        note = phosphodiester linkage is phosphorothioate
source                  1..43
                        mol_type = other DNA
                        organism = synthetic construct
SEQUENCE: 32
gagtaacaga catggaccat cagatctaca agagtagaaa tta             43

SEQ ID NO: 33           moltype = RNA  length = 20
FEATURE                 Location/Qualifiers
```

-continued

```
misc_feature          1..20
                      note = Synthetic Construct
modified_base         1..20
                      mod_base = OTHER
                      note = 2'-O-methyl ribose
source                1..20
                      mol_type = other RNA
                      organism = synthetic construct
SEQUENCE: 33
atctacaaga gtagaaatta                                                   20

SEQ ID NO: 34         moltype = DNA  length = 29
FEATURE               Location/Qualifiers
misc_feature          1..29
                      note = Synthetic Construct
source                1..29
                      mol_type = other DNA
                      organism = synthetic construct
SEQUENCE: 34
gagtaacaga catggaccat cagaattta                                         29
```